(12) United States Patent
Dervan et al.

(10) Patent No.: US 6,673,940 B1
(45) Date of Patent: *Jan. 6, 2004

(54) COMPOSITIONS AND METHODS RELATING TO CYCLIC COMPOUNDS THAT UNDERGO NUCLEOTIDE BASE PAIR-SPECIFIC INTERACTIONS WITH DOUBLE-STRANDED NUCLEIC ACIDS

(75) Inventors: Peter B. Dervan, San Marino, CA (US); Eldon E. Baird, Halfmoon Bay, CA (US)

(73) Assignee: California Institute of Technology, Pasadena, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/479,279

(22) Filed: Jan. 6, 2000

Related U.S. Application Data
(60) Provisional application No. 60/115,232, filed on Jan. 8, 1999.

(51) Int. Cl.[7] .................... C07D 231/02; C07D 403/02; C07H 19/00; C07H 21/02

(52) U.S. Cl. .............................. 548/312.4; 548/312.7; 548/313.1; 548/314.7; 548/334.5; 548/557; 536/22.1; 536/23.1; 536/25.3; 536/25.33; 536/25.6; 536/26.1

(58) Field of Search .......................... 548/312.4, 312.7, 548/313.1, 314.7, 334.5, 557; 536/22.1, 23.1, 25.3, 25.33, 25.6, 26.1

(56) References Cited

U.S. PATENT DOCUMENTS
6,090,947 A * 7/2000 Dervan et al. ........... 518/312.4

FOREIGN PATENT DOCUMENTS
WO  97 30975  8/1997

OTHER PUBLICATIONS

Cho, Design of cyclic polyamides for sequence–specific recognition of the minor groove of DNA. Diss.Abstr. Int. B 1998, 58(7), 3635.*

Dervan, Hairpin and cyclic polyamides for recognition in the minor groove of DNA. Biophysical J. (1996) vol. 70, No. 2, part 2, pp. A11.*

Moser, et al., "Sequence–Specific Cleavage of Double Helical DNA by Triple Helix Formation," *Science* 238, 645–650 (1987).

Duval–Valentin, et al., "Specific Inhibition of Transcription by Triple Helix–forming Oligonucleotides," *Proc. Nat'l. Acad. Sci. USA* 89, 504–508 (1992).

Maher, et al., "Analysis of Promoter–Specific Repression by triple–Helical DNA Complexes in a Eukaryotic Cell–Free Transcription System," *Biochemistry* 31, 70–81 (1992).

Wade, et al., "Design of Peptides That Bind in the Minor Groove of DNA at 5'–(A,T,)G(A,T)C(A,T)–3' Sequences by a Dimeric Sude–By–Side Motif," *J. Am. Chem. Soc.* 114, 8783–8794 (1992).

Mrksich, et al., "Antiparallel Side–by–side Dimeric Motif for Sequence–Specific Recognition in the Minor Groove of DNA by the Designed Peptide 1–methylimidazole–2–carboxamide netrosin," *Proc. Nat'l. Acad. Sci. USA* 89, 7586–7590 (1992).

Trauger, et al., "Recogniton of DNA By Designed Ligands at Subnanomolar Concentrations," *Nature* 382, 559–561 (1996).

White, et al., "Effects of the A•T/T•A Degeneracy of Pyrrole–Imidazole Polymide Recognition in the Minor Groove of DNA," *Biochemistry* 35, 12532–12537 (1997).

White, et al., "On The Pairing Rules for Recognition in the Minor Groove of DNA by Pyrrole–Imidazole Polyamides," *Chem. & Biol.* 4, 569–578 (1997) (1997).

Swalley, et al., "Discrimination of 5'–GCGC–3', 5'–GCGC–3' Sequences in the Minor Groove of DNA by Eight–Ring Hairpin Polymides," *J. Am Chem. Soc.* 119, 6953–6961 (1997).

Turner, et al., "Recognition of Seven Base Pair Sequences in the Minor Groove of DNA by ten–Ring Pyrrole–Imidazole Polyamide Hairpins," *J. Am Chem. Soc.*119, 7636–7644 (1997).

Trauger, et al., "Cooperative Hairpin Dimers for Recognition of DNA by Pyrrole–Imidazole Polyamides," *Agnew Chem. Int. Ed.* 37, 1421–1423 (1997).

Turner, et al., "Aliphatic/Aromatic amino acid Pairings for Polyamide Recognition in the Minor Groove of DNA," *J. Am Chem. Soc.* 120, 6219–6226 (1998).

Kelly, et al., "Binding Site Size Limit of the 2:1 Pyrrole–Imidazole Polyamide–DNA Motif," *Proc. Nat'l. Acad. Sci. USA* 93, 6981–6985 (1996).

Trauger, et al., "Extension of Sequence–Specific Recognition in the Minor Groove of DNA by Pyrrole–Imidazole Polyamides to 9–13 Base Pairs," *J. Am Chem. Soc.* 118, 6160–6166 (1996).

Geirstanger, et al., "Extending the Recognition Site of Desiged Minor Groove Binding Molecules," *Nature Struct. Biol.* 3, 321–324 (1996).

(List continued on next page.)

*Primary Examiner*—Christopher S. F. Low
*Assistant Examiner*—Chih-Min Kam
(74) *Attorney, Agent, or Firm*—Foley & Lardner

(57) ABSTRACT

The design, synthesis, and use of cyclic compounds, including cyclic polyamides, is described. Such compounds comprise at least two polymer portions, one of which comprises at least three molecular units, and the other comprises at least four molecular units. At least one molecular unit of such a compound is a hydrogen bond donor or acceptor. The polymer portions are covalently linked to form a cycle. These compounds are capable of targeting specific nucleotide sequences in double-stranded nucleic acids, particularly double-stranded DNA. Accordingly, such compounds can be used to modulate, e.g., increase or decrease, the expression of one or more genes in vitro or in vivo.

25 Claims, 13 Drawing Sheets

OTHER PUBLICATIONS

Swalley, et al., "A Pyrrole–Imidazole Polyamide Motif for Recognition of Eleven Base Pair Sequences in the Minor Groove of DNA," *Chem. Eur. J.* 3, 1600–1607 (1997).

Tauger, et al., "Recognition of 16 Base Pairs in the Minor Groove of DNA by a Pyrrole–Imidazole Polymide Dimer," *J. Am Chem. Soc.* 120, 3534–3535 (1998).

Gottsfield, et al., "Regulation of Gene Expression by Small Molecules," *Nature* 387, 202–205 (1997).

Cho, et al., "Cyclic Polyamides for Recognition in the Minor Groove of DNA," *Proc. Nat'l. Acad. Sci. USA* 92, 10389–10392 (1995).

Schnolzer, et al., "In Situ Neutralization in Boc–Chemistry Solid Phase Peptide Synthesis," *Int. J. Peptide Protein Res.* 40, 180–193 (1992).

Milton, et al., "Total Chemical Synthesis of a D–Enzyme: The Enantiomers of HIV–1 Protease Show Demonstration of Reciprocal Chiral Substrate Specificity," *Science* 252, 1445–1448 (1992).

Jones, et al., "Control of RNA Initiation and Elongation at the HIV–1 Promoter," *Annu. Rev. Biochem* 63, 717–743 (1994).

Waterman, et al., "Purification of TCF–1α, A T–Cell–Specific Transcription Factor That Activates the T–Cell Receptor Cα Gene Enhancer in a Context–Dependent Manner," *New Biologist* 2, 621–636 (1990).

Kim, et al., "Replication of Type 1 Human Immunodeficiency Viruses Containing Linker Substitution Mutations in the –201 to –130 Region of the Long Terminal repeat," *J. Virol* 67, 1658–1662 (1993).

Sheridan, et al., "Activation of the HIV 1 Enhancer by the LEF–1 HMG Protein on Nucleosome–assembled DNA In Vitro," *Genes Div.* 9, 2090–2104 (1995).

Love, et al., "Structural Basis for DNA bending by the Architectural Transcription Factor LEF–1," *Nature* 376, 791–795 (1995).

Giese, et al., "Assembly and Function of a TCRα Enhancer Complex is Dependent on LEF–1–induced DNA Bending and Multiple Protein–Protein Interactions," *Genes Div* 9, 995–1008 (1995).

Bachelerie, et al., "HIV Enhancer Activity Perpetuated by NF–κB Induction on Infection of Monocytes," *Nature* 350, 709–712 (1991).

Perkins, et al., "An Interaction Between the DNA–Binding Domains of ReIA(p65) and Sp1 Mediates Human Immunodeficiency Virus Gene Activation," *Mol. Cell Biol.* 14, 6570–6583(1994).

Chen, et al., "Assembly of Recombinant TFIID Reveals Differential Coactivator Requirements for Distinct Transcriptional Activators," *Cell* 79, 93–105 (1994).

Maldonado, et al., "News on Initiation and Elongation of Transcription by RNA Polymerase II," *Current Opinion in Cell Biology* 7, 352–361 (1995).

Brunar, et al., "Sequence Composition Effects on the Stabilities of Triple Helix Formation by Oligonucleotides Containing N7–Deoxyguanosine," *Nucleic Acids Res.* 24:11 1987–1991 (1996).

\* cited by examiner

Dimer

5'-AGTACT-3'
3'-TCATGA-5'

(ImPyPyPy-β-Dp)₂

Hairpin

5'-AGTACT-3'
3'-TCATGA-5'

ImPyPyPy-(R)$^{H_2N}$γ-ImPyPyPy-C3-OH cyclo-(γ-ImPyPyPy-(R)$^{H_2N}$γ-ImPyPyPy-)

X=N; cyclo-(γ-ImPyPyPy-(R)^{H_2N}γ-ImPyPyPy-) (3)
X=CH; cyclo-(γ-ImPyPyPy-(R)^{H_2N}γ-PyPyPyPy-) (4)

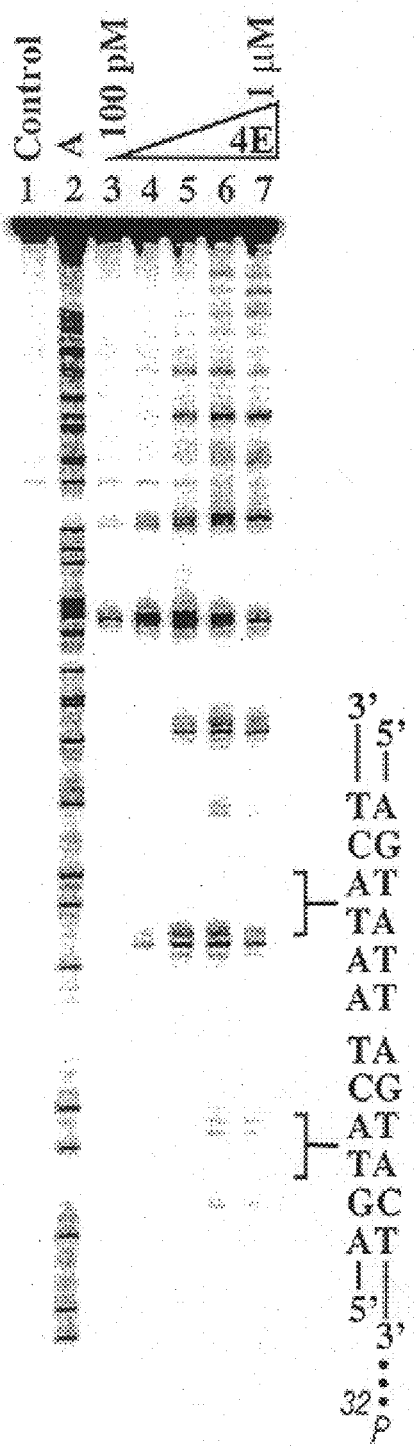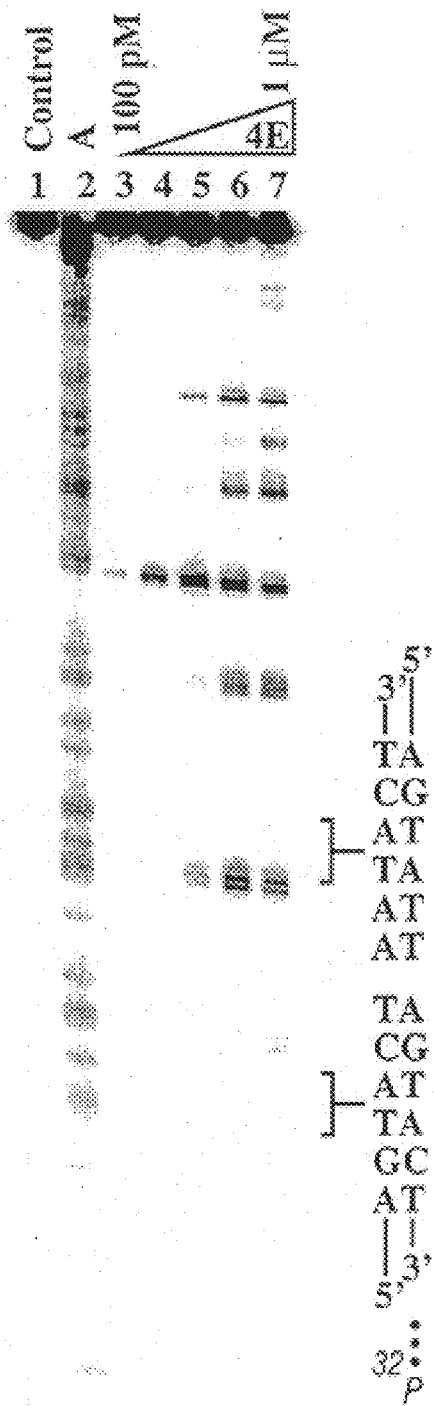
FIG. 6A
FIG. 6B

*4-E·Fe(II)*

*100 nM cyclo- (γ-ImPyPyPy-(R)$^{EDTA}$γ-PyPyPyPy)* ically, an Im/Py pair in adjacent polymers was fond to
COMPOSITIONS AND METHODS RELATING TO CYCLIC COMPOUNDS THAT UNDERGO NUCLEOTIDE BASE PAIR-SPECIFIC INTERACTIONS WITH DOUBLE-STRANDED NUCLEIC ACIDS

RELATED APPLICATION

This application claims the priority of United States Provisional Application No. 60/115,232, entitled "Compositions and Methods Relating to Cyclic Compounds that Undergo Nucleotide Base Pair-Specific Interactions with Double-Stranded Nucleic Acids", filed Jan. 8, 1999, which is incorporated by reference herein in its entirety including drawings.

U.S. GOVERNMENT RIGHTS

The U.S. Government has certain rights in this invention pursuant to Grant No. GM-27681 awarded by the National Institutes of Health.

FIELD OF THE INVENTION

This invention relates to cyclic compounds that undergo nucleotide base pair-specific interactions with double stranded nucleic acids. The invention also concerns methods of using such cyclic compounds, as well as methods relating to their solid state synthesis.

BACKGROUND OF THE INVENTION

None of the following discussion of the background of the invention, which is provided solely to aid the reader in understanding the invention, is admitted to be or to describe prior art to the invention.

The design of synthetic ligands capable of reading information stored in the DNA double helix has been a long-standing goal of chemistry and molecular biology. Cell-permeable small molecules, which target predetermined nucleotide sequences in double-stranded nucleic acids, particularly double-stranded DNA (dsDNA), are useful in regulating, or modulating, gene-expression. Oligodeoxynucleotides that recognize the major groove of double-helical DNA via triple-helix formation bind to a broad range of sequences with high affinity and specificity. See Moser, et al., *Science*, vol. 238:645–650 (1987), Duvalvalentin, et al., *Proc. Nat'l Acad. Sci. USA*, vol. 89:504–508 (1992), Maher, et al., *Biochemistry*, vol. 31:70–81 (1992). Although oligonucleotides and their analogs have been shown to interfere with gene expression, the triple helix approach so far has been limited to purine tracks and suffers from poor cellular uptake.

Another recent approach to targeting specific nucleotide sequences in dsDNA has involved molecules known as "polyamides." See U.S. Ser. No. 08/607,078, PCT/US97/03332, U.S. Ser. Nos. 08/837,524, 08/853,525, PCT/US97/12733, U.S. Ser. No. 08/853,522, PCT/US97/12722, PCT/US98/06997, PCT/US98/02444, PCT/US98/02684, PCT/US98/01006, PCT/US98/03829, and PCT/US98/0714. As described in the foregoing references, polyamides comprise polymers of amino acids covalently linked by amide bonds. Preferably, the amino acids used to form these polymers include N-methylpyrrole (Py) and N-methylimidazole (Im).

Wade, et al. (*J. Am. Chem. Soc.*, vol. 114:8783–8794 (1992)) reported the design of polyamides that bind in the minor groove of dsDNA at 5'-(A,T)G(A,T)C(A,T)-3' sequences by a dimeric, side-by-side motif; Mrksich, et al. (*Proc. Natl. Acad. Sci. USA*, vol. 89:7586–7590 (1992)), reported an antiparallel, side-by-side polyamide motif for sequence-specific recognition in the minor groove of dsDNA by the designed peptide 1-methylimidazole-2-carboxamide netropsin; and Trauger, et al. (*Nature*, vol. 382:559–561 (1996)) reported the recognition of a targeted dsDNA by a polyamide at subnanomolar concentrations. The particular order of amino acids in such polyamides, and their pairing in dimeric, antiparallel complexes formed by association of two polyamide polymers, determines the sequence of nucleotides in dsDNA with which the polymers preferably associate.

The development of pairing rules for minor groove binding polyamides derived from N-methylpyrrole (Py) and N-methylimidazole (Im) amino acids provided a useful code to control target nucleotide base pair sequence specificity. Specifically, an Im/Py pair in adjacent polymers was fond to distinguish G•C from C•G and both of these from A•T or T•A base pairs. A Py/Py pair was found to specify A•T from G•C but could not distinguish A•T from T•A. White, et al. (*Biochemistry*, vol. 35:12532–12537 (1996)) reported the effects of the A•T/T•A degeneracy of Py/Im polyamide recognition in the minor groove of dsDNA. White, et al. (*Chem. & Biol.* vol. 4:569–578 (1997)) reported the pairing rules for recognition in the minor groove of dsDNA by Py/Im polyamides and the 5'→3', N→C orientation preference for polyamide binding in the minor groove of dsDNA.

More recently, it has been discovered that inclusion of a new aromatic amino acid, 3-hydroxy-N-methylpyrrole (Hp) (made by replacing a single hydrogen atom in Py with a hydroxy group), in a polyamide and paired opposite Py enables A•T to be discriminated from T•A by an order of magnitude. Utilizing Hp together with Py and Im in polyamides provides a code to distinguish all four Watson-Crick base pairs (i.e., A•T, T•A, G•C, and C•G) in the minor groove of dsDNA, as described in Table 1.

TABLE 1

| | Pairing Code for Minor Groove Recognition | | | |
|---|---|---|---|---|
| Pair | G · C | C · G | T · A | A · T |
| Im/Py | + | – | – | – |
| Py/Im | – | + | – | – |
| Hp/Py | – | – | + | – |
| Py/Hp | – | – | – | + |

Favored (+), disfavored (–)

As discussed above, a number of different polyamide motifs have been reported in the literature, including "hairpins," "H-pins," "overlapped," "slipped," and "extended" polyamide motifs. Specifically, hairpin polyamides are those wherein the carboxy terminus of one amino acid polymer is linked via a linker molecule, typically aminobutyric acid or a derivative thereof to the amino terminus of the second polymer portion of the polyamide. Indeed, the linker amino acid γ-aminobutyric acid (γ), when used to connect first and second polyamide polymer portions, or polyamide subunits, C→N in a "hairpin motif," enables construction of polyamides that bind to predetermined target sites in dsDNA with more than 100-fold enhanced affinity relative to unlinked polyamide subunits. See Trauger, et al., *Nature*, vol. 382:559–561 (1996), Swalley, et al., *J. Am. Chem. Soc.*, vol. 119:6953–6961 (1997), Turner, et al., *J. Am. Chem. Soc.*, vol. 119:7636–7644 (1997), Trauger, et al., *Angew. Chemie. Int. Ed. Eng.*, vol. 37:1421–1423 (1997), Turner, et al., *J. Am. Chem. Soc.*, vol. 120:6219–6226 (1998), Kelly, et al., *Proc.*

Nat'l Acad. Sci. USA, vol. 93:6981–6985 (1996), Trauger, et al., *J. Am. Chem. Soc.*, vol. 118:6160–6166 (1996), Geierstanger, et al., *Nature Struct. Biol.*, vol. 3:321–324 (1996), Swalley, et al., *Chem. Eur. J.*, vol. 3:1600–1607 (1997), and Trauger, et al., *J. Am. Chem. Soc.*, vol. 120:3534–3535 (1998). Moreover, eight-ring hairpin polyamides (comprised of two four amino acid polymer portions linked C→N) have been found to regulate transcription and permeate a variety of cell types in culture. See Gottesfield, J. M.; et al., *Nature*, vol. 387:202–205 (1997).

An H-pin polyamide motif, i.e., wherein two paired, antiparallel polyamide subunits are linked by a linker covalently attached to an internal polyamide pair, have also been reported. Another polyamide motif that can be formed between linked or unlinked polyamide subunits is an "extended" motif, wherein one of the polyamide subunits comprises more amino acids than the other, and thus has a single-stranded region. See U.S. Ser. No. 08/607,078. In contrast, an "overlapped" polyamide is one wherein the antiparallel polyamide subunits completely overlap, whereas in a "slipped" binding motif, the two subunits overlap only partially, with the C-terminal portions not associating with the N-terminal regions of the other subunit. See U.S. Ser. No. 08/607,078.

The literature has also reported the synthesis of a six-ring Py/Im-containing cyclic polyamide (cyclo-(Im-Py-Py-γ-Py-Py-Py-γ)) that bound its designated five base pair (bp) dsDNA target sequence (5'-TGTTA-3') at subnanomolar concentrations, and with 40-fold higher affinity relative to a hairpin analog (Im-Py-Py-γ-Py-Py-Py-Dp) containing the same amino acid pairings. See Cho, et al., *Proc. Nat'l Acad. Sci. USA*, vol. 92:10389–10392 (1995). It was postulated that closing the ends of the hairpin to form a cyclic compound would restrict conformational space for the DNA-binding molecule. Significantly, however, the hairpin analog more strongly bound to its match sequence versus single base pair mismatch sites by a factor of 20, whereas the cyclic polyamide bound match versus mis-matched sites with only 4–17-fold specificity, suggesting that an energetic price was paid by forming a cyclic molecule which had more restricted conformational flexibility as compared to non-cyclic polyamide motifs. Because of the discouraging thermodynamics of cyclic polyamides with regard to sequence specificity, cyclic polyamides appear to not have been investigated further, although the solid state synthesis of an 8-ring cyclic polyamide, cyclo-(Im-Py-Im-Py-γ-Im-Py-Im-Py-(G-Dp)-γ) was reported in PCT/97US/03332, as were the sequences of two apparently prophetic 8-ring cyclic polyamides. These sequences were cyclo(Im-Py-Im-Py-γ-Im-Py-Im-Py-(G-Dp)) and cyclo(Im-Py-Py-Py-γ-Im-Py-Py-Py-(G-Dp)). No biochemical characterization, e.g., target sequence binding affinity or sequence specificity, was provided for any of these three cyclic polyamides.

SUMMARY OF THE INVENTION

The present invention is based on the surprising and unexpected discovery of new and useful cyclic compounds, including cyclic polyamides, that interact in a nucleotide base pair-specific manner with desired target sequences in double-stranded nucleic acid molecules, particularly dsDNA, with affinities and specificities comparable to or better than naturally occurring DNA-binding proteins.

One aspect of the invention concerns cyclic compounds having molecular structures under physiological conditions that enable nucleotide base pair-specific interactions to be formed with high affinity and specificity with double-stranded nucleic acid molecules. Preferably, such molecules have an affinity for a specific sequence of nucleotide base pairs that is less than about 100 nM, preferably less than about 10 nM, and even more preferably, less than about 1 nM, as measured by DNase footprint titration See PCT/US97/03332. Similarly, such compounds have a sequence specificity, or prefer to bind to one sequence, the target sequence, by a factor of greater than about 2, preferably greater than about 5, and even more preferably greater than about 10, as compared to a sequence that differs by one nucleotide base pair.

Another aspect of the invention concerns cyclic compounds that contain at least seven units, at least one of which is a hydrogen bond donor or acceptor, configured in a cycle to form a molecular structure that interacts with specific nucleotide base pairs in a double-stranded nucleic acid molecule under physiological conditions. Specifically excluded from the cyclic compounds according to the invention are three cyclic polyamides having the following amino acid sequences: cyclo-(Im-Py-Im-Py-γ-Im-Py-Im-Py-(G-Dp)-γ), cyclo(Im-Py-Im-Py-γ-Im-Py-Im-Py-(G-Dp)), and cyclo(Im-Py-Py-Py-γ-Im-Py-Py-Py-(G-Dp)).

A "cycle" is a compound composed of covalently linked independent molecular units at least one of which is covalently linked directly (i.e., without a linker) or indirectly (i.e., through a linker) to at least two other independent molecular units of the cycle. A "covalent linkage" refers to a chemical bond involving the sharing of one or more electrons between two or more atoms, and an "independent molecular unit" or "unit" refers to a previously synthesized molecule that is incorporated into the cyclic compound during the latter compound's synthesis. Preferred independent molecular units include, but are not limited to, molecules that are hydrogen bond donors or hydrogen bond acceptors, or molecules which become hydrogen bond donors or acceptors following incorporation into a cyclic compound according to the invention. Other preferred molecular units include amino acids, nucleosides, and carbohydrates.

A "hydrogen bond donor" refers to a molecule or group of atoms including a hydrogen atom covalently linked to one electronegatively charged atom such that the hydrogen atom becomes electropositively charged and can thus be electrostatically attracted to interact with a second electronegative atom or group of atoms (in either case, the hydrogen bond acceptor). Representative hydrogen bond donors include a hydrogen covalently bonded to a nitrogen in an amide bond, and the 2-amino group of guanine. Representative hydrogen bond acceptors include the N3 of purines and Im, and the O2 of pyrimidines in dsDNA.

A "nucleotide-specific interaction" refers to a non-covalent interaction between a hydrogen bond donor or acceptor of a cyclic compound and a hydrogen bond acceptor or donor of nucleotide base in a double-stranded nucleic acid to form at least one hydrogen bond between a hydrogen bond donor or acceptor of a cyclic compound according to the invention with at least one of the nucleotides of a Watson-Crick base pair in a double-stranded nucleic acid. Preferably, at least one hydrogen bond is formed between each donor/donor or donor/acceptor pair of a cyclic compound and the adjacent nucleotide pair in the target sequence of the double-stranded nucleic acid, particularly dsDNA. A "donor/donor pair" or a "donor/acceptor pair" refers to a pair of hydrogen bond donors, or a hydrogen bond donor and acceptor, of a cyclic compound which reside on different polymer portions thereof but which are located proximate to one another in the cyclic compound such that each member of the pair interacts with a different member of the Watson-Crick nucleotide base pair with which one or both members of the donor/donor or donor/acceptor pair form one or more hydrogen bonds.

In preferred embodiments, a "cyclic compound" refers to a compound that has two or more polymer portions or subunits, each of which polymer portions or subunits itself comprises multiple units at least one of which is a hydrogen bond donor or acceptor. In these embodiments, at a minimum the cyclic compound comprises two polymer portions. The first polymer portion comprises a polymer of at least three units, one or more of which acts as either a hydrogen bond donor or hydrogen bond acceptor. The second polymer portion comprises a polymer of at least four units, at least one of which also acts as either a hydrogen bond donor or hydrogen bond acceptor. The units which act as hydrogen bond or acceptors in either of the first or second polymers portions may be covalently linked to one another in a particular polymer, or they be separated by one or more intervening moieties, for example, a moiety which serves to restore the binding register to the cyclic compound. "Binding register" refers to the alignment of hydrogen bond donors and acceptors of a polymer portion with their respective hydrogen bond acceptors and donors on one strand of a double-stranded nucleic acid. Preferred examples of such register restoring moieties include β-alanine ("β"), glycine, and other aliphatic chains which provide proper spacing between flanking hydrogen bond donors and/or acceptors of a polymer portion so as to enable hydrogen bond formation with corresponding hydrogen bond acceptors and donors of a strand of the double-stranded target nucleic acid.

To form a cyclic compound, the first and second polymer portions are attached at two or more locations, directly by covalent bonds between the polymers themselves, or indirectly, such as through the use of one or more linker molecules, or by a combination of direct and indirect attachment. As those in the art will appreciate, the resulting cyclic molecule may be symmetrical, in that each of the units (e.g., a hydrogen bond donors or acceptor) of one polymer portion align with a unit (e.g., a hydrogen bond donor or acceptor) of the other polymer portion. Alternatively, the cyclic compound may be asymmetrical, wherein at least one unit of one polymer portion does not align with a unit of the other polymer portion under physiological conditions in the presence of dsDNA.

In certain preferred embodiments of this aspect of the invention, at least one of the units, e.g., a hydrogen bond donor or acceptor, is an amino acid. An "aminoacid" refers to any naturally occurring or synthetic molecule having an amino group, a carboxyl group, and an R group attached to the same or a different carbon atom. Representative examples of amino acids useful in the practice of this invention include the L- and D-forms of the twenty amino acids assembled into proteins in animals and plants, other aliphatic and aromatic amino acids, including pyrrole, hydroxypyrrole, and imidazole, and any chemical modifications or derivatives of any of the foregoing. Amino acids may serve as hydrogen bond donors (e.g., Py), hydrogen bond acceptors (e.g., Im), as register restoring moieties (also referred to herein as "springs"), or as linkers. Particularly preferred for hydrogen bond formation are aromatic amino acids. An "aromatic amino acid" is one wherein the R group comprises a ring having four or more members, preferably 5 or 6 members. In particularly preferred embodiments, the members of the ring members are independently selected from the group consisting of carbon, nitrogen, sulfur, and oxygen.

In other preferred embodiments, at least two of the hydrogen bond donors and/or acceptors of a polymer portion are covalently attached by an amide bond. Such cyclic compounds are referred to herein as cyclic polyamides. In certain particularly preferred embodiments, the first and second polymer portions comprise the same number of units, wherein a "unit" is a molecule that provides proper nucleotide-to-nucleotide spacing for a polymer of such units such that a hydrogen bond-stabilized non-covalent complex can be formed under physiological conditions between hydrogen bond donors and/or acceptors in the polymer and targeted hydrogen acceptors and/or donors in an adjacent nucleic acid strand of a double-stranded nucleic acid. Clearly, not all units within a polymer need to be hydrogen bond donors or acceptors, but each unit should provide spacing such that desired hydrogen bond formation can occur between specific hydrogen bond donors and/or acceptors in the polymer portion and corresponding hydrogen bond acceptors and/or donors in the nucleic acid strand with which the polymer forms a non-covalent complex. However, the polymer must contain a sufficient number of such units that are hydrogen bond donors or acceptors to enable hydrogen bond-stabilized non-covalent complex formation between a polymer of such units and a strand of a double-stranded nucleic acid.

The polymer portions, when linked to form cyclic compounds, may exhibit symmetrical motifs (e.g., an "overlapped" motif) or asymmetrical motifs (e.g., "slipped" or "extended" motifs). In preferred embodiments, the polymer portions each comprise the same number of units, and may or may not contain the same number of hydrogen bond donors or acceptors. In particularly preferred embodiments, each polymer portion comprises 4, 5, 6, 7, 8, 9, 10, 11, 12, 13, 14, 15, 16, 17, 18, 19, or 20 units.

Certain preferred embodiments of this aspect of the invention concern polyamides, wherein each unit of the first and second polymer portions is an amino acid, preferably linked by amide bonds. Particularly preferred are those wherein each polymer portion comprises 4, 5, 6, 7, 8, 9, 10, 11, 12, 13, 14, 15, 16, 17, 18, 19, or 20 amino acids, some, and preferably all, of which are selected from the group consisting of Py, Hp, Im, β, and glycine. In some of these embodiments, the first and second polymer portions comprise equal numbers of amino acids, the particular order of which determines the nucleotide base pairs with which the cyclic compound will preferentially interact. When each polymer portion comprise an equal number of amino acids, a cyclic polyamide may have an "overlapped" or "slipped" binding motif. In other embodiments, each polymer portion comprises a different number of amino acids. Thus, the cyclic compound will typically have an "extended" binding motif.

In many embodiments, the invention concerns cyclic compounds wherein each unit of the first polymer portion aligns with a unit of the second polymer portion to form a unit pair that preferably associates under physiological conditions with at least one, but not all, nucleotide base pairs selected from the group consisting of A/T, T/A, G/C, or C/G. A "unit pair" refers to two units, one from each of two different polymer portions, the align in a cyclic compound such that upon interaction with a double-stranded nucleic acid, each unit of the pair interacts (or if no interaction, aligns) with a different nucleotide in a Watson-Crick nucleotide base pair in a double-stranded nucleic acid. For example, if the unit pair interacts at A/T base pair, one unit of the unit pair interacts or otherwise aligns with A and the other unit aligns with T. Preferably, the unit pair preferably associates with at least one, but not all, of the four Watson-Crick base pairs (A/T, T/A, G/C, and C/G in dsDNA, and A/U, U/A, G/C, and C/G in RNA:DNA and RNA:RNA duplexes), thereby providing some level of sequence specificity. For example, it is known that Py/Py unit pairs prefer A/T or T/A base pairs in dsDNA, but not G/C or C/G base pairs. Particularly preferred are unit pairs that prefer one nucleotide base pair to the other three possible in a particular type double-stranded nucleic acid. For example, a Im/Py unit pair prefers G/C to the other three base pairs, whereas a Py/Im unit pair prefers C/G above the other three possibilities.

"Physiological conditions" refer to conditions found in vivo, or, alternatively, to in vitro reaction conditions intended to mimic or approximate those found in vivo. With regard to in vitro conditions which seek to approximate in vivo conditions, consideration should be given to pH, salt concentrations, buffering capacity, temperature, and such other parameters as may be deeded necessary in the particular circumstance. For purposes of illustration, physiological conditions in the context of interactions between acyclic compound according to the invention and dsDNA include those which are suitable for performing in vitro experiments which exploit the in vivo activity of an enzyme, for example, a DNA polymerase, an RNA polymerase, or an enzyme which modifies nucleic acids. Preferably, such enzymes will have at least 50%, more preferably, at least about 75%, and even more preferably, at least about 90%, of their optimal activity under the experimental conditions selected. As those in the art will appreciate, what constitutes physiological conditions in a given situation may depend on many factors, such as the type of organism being considered, the environment inhabited by the organism, etc.

In various embodiments of this aspect of the invention, a cyclic compound comprises at least one linker molecule. When used herein, "linker" refers to a molecule used to covalently link two polymer portions of a cyclic compound. Preferably, two linkers are employed, although it may be desirable to include 1, 2, 3, or more additional linkers. Preferred linkers are those which comprise an aliphatic chain, for example, β, glycine, and aminobutyric acid, with the latter being particularly preferred. Preferred cyclic compounds comprise two linkers comprising aliphatic chains, especially aminobutyric acid. Particularly preferred aminobutyric acids include γ-aminobutyric acid, particularly substituted derivatives thereof, for example, (R)-2,4-diaminobutyric acid. Linkers may be used to link terminal units of polymer portions to one another, or a terminal unit of one polymer to an internal unit of another polymer portion. Alternatively, linkers may be used to join two polymer portions by covalent linkages between internal units of each polymer portion.

Another aspect of the invention concerns a cyclic compound functionally associated (preferably by a covalent linkage) with an independent compound. Independent compounds can be any compound, with other cyclic compounds, proteins, nucleic acids, and polyamides (e.g., a polyamide molecule having a hairpin, H-pin, extended, overlapped, or slipped polyamide motif) being preferred.

The cyclic compounds of the invention interact with double-stranded nucleic acid with varying degrees of binding affinity and sequence specificity, depending on various factors, including compound size and composition, the targeted nucleotide base pair sequence, nucleic acid type, etc. Preferably, a cyclic compound will interact with its target nucleotide base pair sequence with an affinity, as measured by DNase footprint titration, of less than about 100 nM, preferably less than about 10 nM, more preferably less than about 1.0 nM, even more preferably less than about 0.1 nM. With regard to specificity (as measured in vitro under physiological conditions by comparing binding between a compound's intended target sequence, i.e., a "match" site, and a test site equivalent to the target sequence except for a one nucleotide base pair difference, i.e., a "single base pair mismatch" site), a cyclic compound of the invention should have at least about two-fold, preferably about 3–5 fold, more preferably 5–10-fold, and even more preferably greater than about 10-fold specificity for its match versus single base pair mismatch site.

When the double-stranded nucleic acid is dsDNA, cyclic compounds according to the invention may target specific molecular structures, for example, the major or minor groove, associated with a target nucleic acid sequence. Preferred cyclic compounds are those which interact with structures in the minor groove of dsDNA in the B-form. Cyclic polyamide compounds represent a particularly preferred class of such compounds.

Structurally, the cyclic compounds of the invention can be envisioned as comprising first and second polymer portions having the following formulas:

First polymer portion:

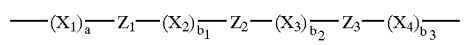

wherein $a \geq 0$ and $b_1$, $b_2$ and $b_3 \geq 1$, $x_1$, $x_2$, $x_3$, and $x_4$ are units, one or more of which serve as hydrogen bond donors or acceptors, and one or more of which may be the same or different molecules, and $z_1$, $z_2$, and $z_3$ each is a covalent linkage between adjacent units.

Second polymer portion:

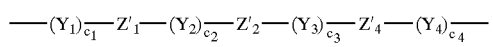

wherein $c_1$, $c_2$, $c_3$ and $c_4 \geq 1$, $y_1$, $y_2$, $y_3$, and $y_4$ each are units, one or more of which serve as hydrogen bond donors or acceptors, and one or more of which may be the same or different molecules, and $z'_1$, $z'_2$, and $z'_3$ each is a covalent linkage between adjacent units. In preferred embodiments, $x_2$, $x_3$, and $x_4$ and $y_2$, $y_3$, and $y_4$ form unit pairs that each preferably interact with at least one, but not all, Watson-Crick nucleotide base pairs, most preferably with only one such nucleotide base pair. The first and second polymer portions also typically comprise two termini. When the cyclic compound is a cyclic polyamide, one such terminus is an amino terminus, the other is a carboxy terminus. In particularly preferred embodiments, when contained in a cyclic polyamide, the polymer portions are arrayed in an anti-parallel manner.

Another aspect of the invention concerns pharmaceutical compositions comprising a cyclic compound according to the invention and a pharmaceutically acceptable carrier. Such compositions can be formulated into liquid or solid forms, and can be delivered by any appropriate route of administration. Preferred liquid formulations are aqueous solutions, suspension, slurries, gels, and emulsions. Preferred solid forms include pills, capsules, and powders (including lyophilized powders). Preferred routes of administration include parenteral (e.g., subcutaneous, intramuscular, intravenous, and interperitoneal) injection, transdermal delivery, inhalation, and oral delivery. Such compositions may also include additional components, for example, one or more other biologically active ingredients, liposomes (such as may be formed from various cationic lipids), etc. Such compositions may also be able to target delivery of a cyclic compound according to the invention to one or more particular cell or tissue types, or, with respect to eukaryotic cells, to an intracellular compartment containing double-stranded nucleic acid, e.g., a cell's nucleus (such as by complexing the cycle with a nuclear localization signal).

Other aspects relate to methods of using the compounds according to the invention. One area of application relates to the modulation of gene expression. "Modulation" refers to activating, increasing, enhancing, derepressing, reducing, decreasing, inhibiting, or preventing expression of a gene. Thus, some cyclic compounds positively affect, or up-regulate, gene expression, while others negatively affect, or down regulate, gene expression. A "gene" refers to genetic locus that encodes one or more gene products. As those in the art will appreciate, a gene can encode more than one gene product by virtue of differential mRNA splicing. Gene products include proteins (e.g., enzymes, receptors, antibodies, growth factors, and hormones) and RNA molecules, particularly tRNAs, ribosomal RNAs and other RNAs which are subunits of multi-component complexes (e.g., telomerase), and catalytic RNAs (e.g., ribozymes). To achieve the desired level of modulation in systems comprising cells, it is necessary to deliver a sufficient quantity of a cyclic compound according to the invention to the cells.

In some embodiments, the use of cyclic compounds according to the invention can modulate the expression of more than one gene. For example, more than one cyclic compound, each of which specifically modulates a particular gene, can be delivered. Alternatively, the cyclic compound may directly influence the expression of more than one gene. For example, if the cyclic compound targets a nucleotide base pair sequence found in a regulatory region of more than one gene, modulation of expression of multiple genes may occur. Alternatively, the cyclic compound may exhibit its expression-modulating effects indirectly, or by a combination of direct and indirect effects. For instance, if the cycle inhibits expression of a phosphatase that removes phosphates from a plurality of proteins, the expression of genes regulated by pathways that involve the phosphatase will be affected.

Certain embodiments of this aspect concern modulation of gene expression in vitro. "In vitro" includes both in situ and cell-free environments (e.g., a cell extract or in a well-defined reaction medium). Thus, the compounds of the invention can be used to modulate gene expression in cultured cells, such as may be used in ex vivo therapy or research.

Other embodiments of this aspect relate to the modulation of gene expression in vivo, some of which concern therapeutic purposes. As used herein, a "therapeutic purpose" includes both therapy (i.e., treatment of an existing condition) and prophylaxis (i.e., prevention). Representative examples of a therapeutic purpose include treatment of a disease associated with aberrant expression of the gene of interest (as occurs in certain cancers and genetic diseases, for example), as well as treatment of a disease associated with the presence of a pathogen (e.g., a virus or a bacterial or eukaryotic pathogenic organism).

Cyclic compounds according to the invention can be used for therapeutic purposes in conjunction with a vast array of organisms, including both animals and plants. Preferred animals amenable to application of the therapeutic and prophylactic methods herein described include animals of agricultural importance, for example, avian (particularly poultry), bovine, equine, ovine, and porcine animals, companion animals such as dogs and cats, and humans. With regard to plants, preferred plants include those of agricultural importance, including cereals, grains, and grasses. Similarly, cyclic compounds according to the invention can be developed to control pests, e.g., certain insects and rodents.

Yet other aspects of the invention concerns methods for the solid phase synthesis of one or more cyclic polyamides. Such methods comprise providing a solid support (e.g., a polystyrene resin), protecting and activating the appropriate carboxamide monomers and/or dimers, sequentially adding the carboxamide monomers and/or dimers to the solid support, beginning with the carboxy terminal carboxamide residue, deprotecting the carboxamides following formation of the desired polyamide, releasing the polyamide from the solid support, and cyclizing the polyamide to form a cyclic polyamide. The resulting cyclic polyamide may then be purified, e.g., by reverse phase HPLC. Preferably, such purification results in a cyclic compound that has a purity of more than about 90%, preferably more than about 95%, particularly more than about 99%.

BRIEF DESCRIPTION OF THE DRAWINGS

FIGS. 6A and 6B show the results of affinity cleaving experiments using cyclo-(γ-Im-Py-Py-Py-(R)$^{EDTA-Fe(II)}$γ-Py-Py-Py-Py) (4-E•Fe(II)) on the (a) 3'- and (b) 5'-$^{32}$P-labeled 229 bp restriction fragment of pJT8. The match and single mis-match sites 5'-AGTATT-3' and 5'-AGTACT-3' are shown on the right side of the autoradiograms. The lanes of each gel are described as follows lane 1, intact DNA (control); lane 2, A reaction; lanes 3–7, 100 pM, 1 nM, 10 nM, and 100 nM, and 1 μM polyamide, respectively. All lanes contain 15 kcpm of either 3'- or 5'-radiolabeled DNA, 20 mM HEPES buffer (pH 7.3), 200 mM NaCl, 50 μg/ml glycogen, 5 mM DTT, 1 μM Fe(II), pH 7.0, and were run at 22° C.

Figures 1A, 1B:
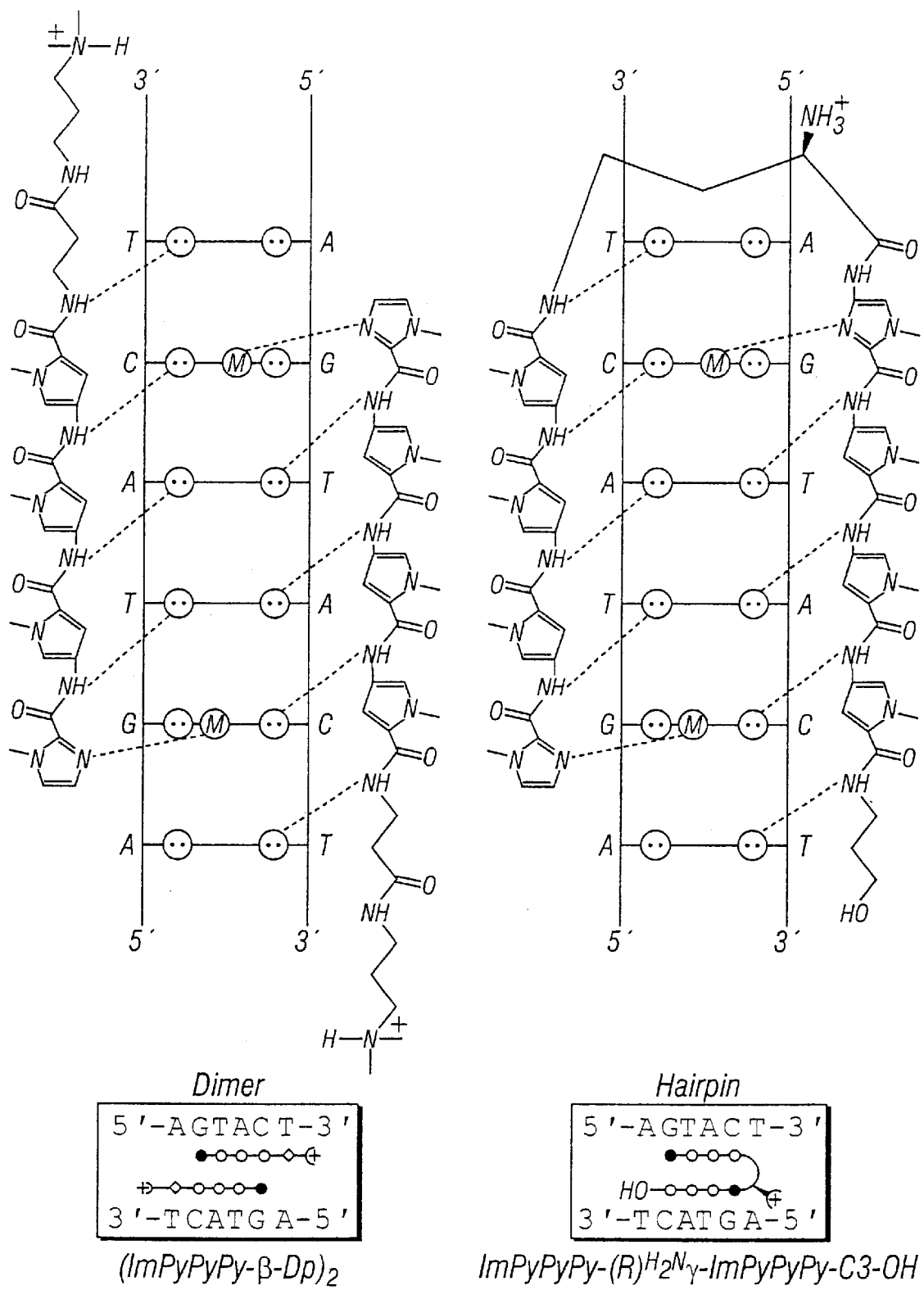
FIGS. 1A–1C (top panel, a–c) shows hydrogen bonding models of the polyamide-dsDNA complexes formed between the 2:1 dimer of the polyamide Im-Py-Py-Py-β-Dp (1), the 1:1 hairpin Im-Py-Py-Py-(R)$^{H2N}$γ-Im-Py-Py-Py-OH (2), and the 1:1 cyclic polyamide cyclo-(γ-Im-Py-Py-Py-(R)$^{H2N}$γ-Im-Py-Py-Py) (3) with its 6 bp match site, 5'-AGTACT-3'. Circles with dots represent lone pairs of the N3 of purines and the O2 of pyrimidines in the dsDNA. Circles containing an H represent the N2 hydrogen of guanine. Predicted hydrogen bonds are illustrated by dotted lines.
Figure 1C:
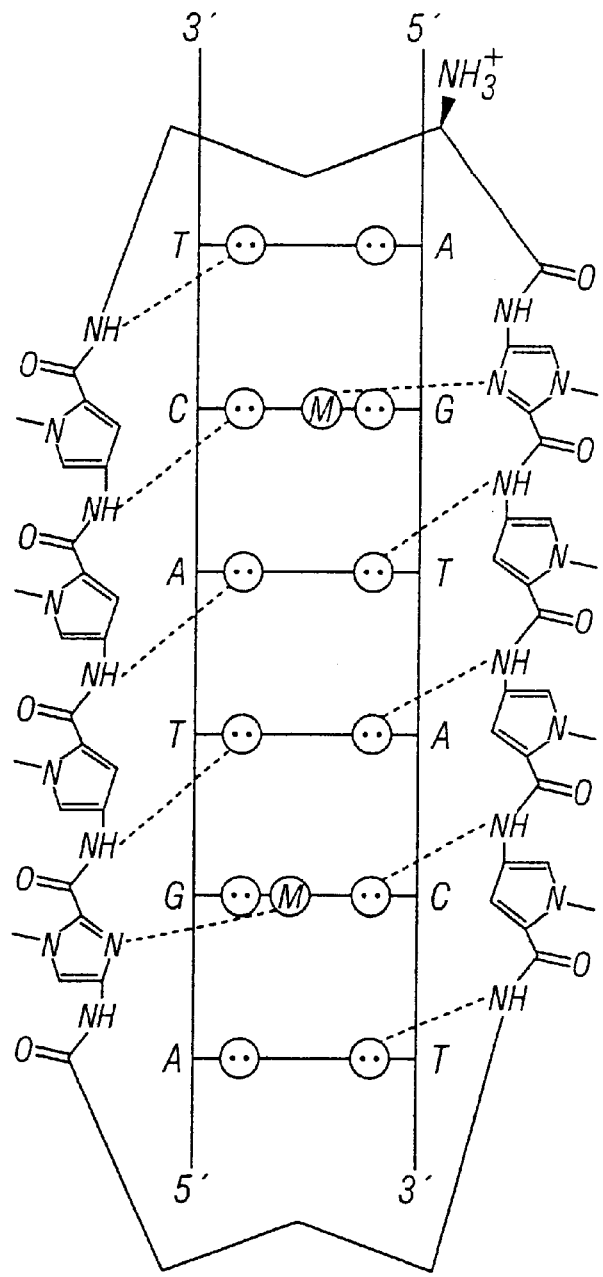
Figure 1C:
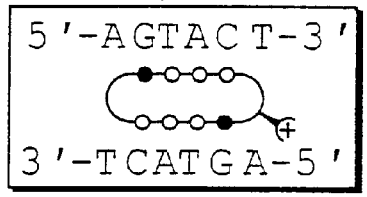
Figure 2A:
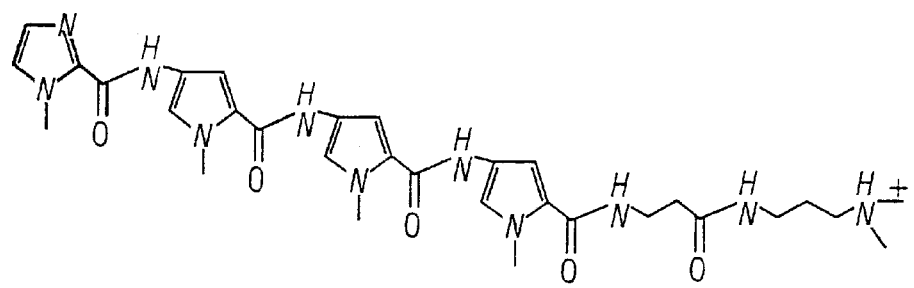
FIGS. 2A–2D show the structures of the eight-ring polyamides Im-Py-Py-Py-β-Dp (1), Im-Py-Py-Py-(R)$^{H2N}$γ-Im-Py-Py-Py-OH (2), cyclo-(γ-Im-Py-Py-Py-(R)$^{H2N}$γ-Im-Py-Py-Py) (3), and cyclo-(γ-Im-Py-Py-Py-(R)$^{H2N}$γ-Py-Py-Py-Py) (4) as synthesized by solid phase methods.
Figure 2B:
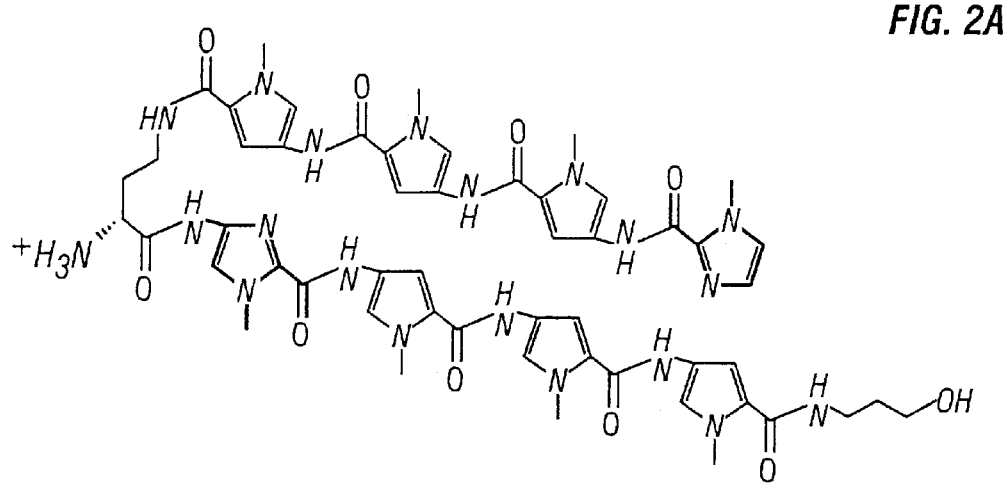
Figure 2C:
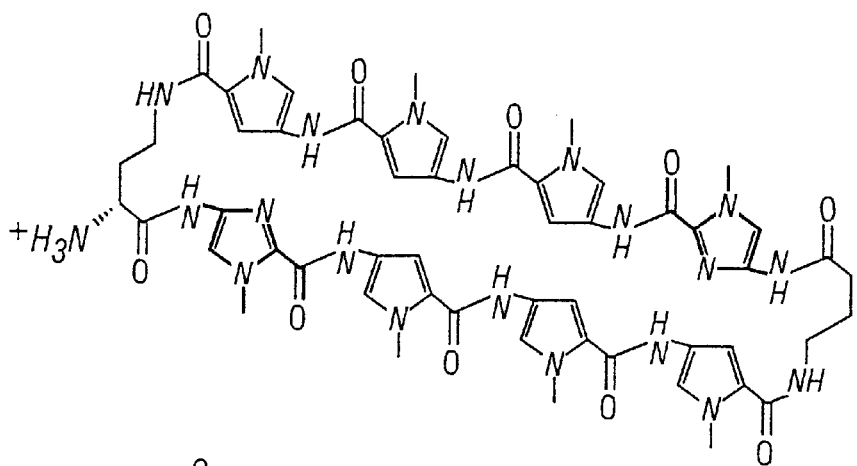
Figure 2D:
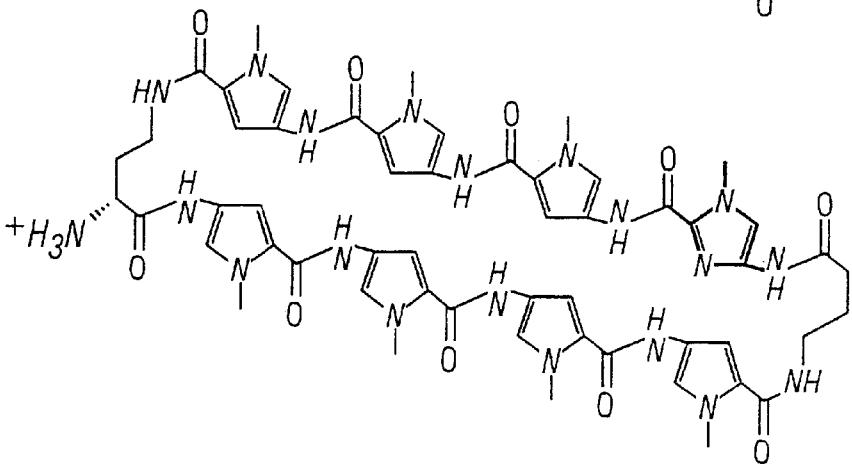

Other features and advantages of the invention will be apparent from the following description of the preferred embodiments thereof, and from the claims.

DETAILED DESCRIPTION OF THE INVENTION

The present invention is based on the surprising discovery that synthetic cyclic compounds comprising more than six units, one or more of which of which acts as a hydrogen bond donor or acceptor, can be constructed so as to produce molecules having three dimensional structures that form nucleotide base-pair specific interactions with double-stranded nucleic acids. The design, synthesis, and use of such compounds is described in detail below.

I. Cyclic Compounds

A. Generic Description of Cyclic Compounds

The present invention concerns cyclic compounds, or cycles, that interact with high affinity, e.g., subnanomolar affinity, and specificity with specific double-stranded nucleotide sequences. Broadly, cycles according to the invention comprise at least seven covalently linked units (i.e., independently synthesized molecules) at least one of which is covalently attached directly or indirectly to at least two other units of the compound. Nucleotide base pair specificity is provided by the particular three-dimensional structure of the particular cycle, which structure is dictated by the type and configuration of units incorporated into the compound. The unit composition and three-dimensional structure of such compounds specifies what type of interactions (e.g., hydrogen bonds) will occur with a specific sequence of nucleotide base pairs.

Preferably, cyclic compounds according to the invention provide a molecular scaffold that directs the formation of specific electrostatic and non-electrostatic interactions with a target nucleotide sequence. Particularly preferred interactions are hydrogen bonds, which are non-covalent electrostatic interactions formed between a hydrogen bond and hydrogen bond acceptor. Representative hydrogen bond donors include amide hydrogen and the 2-amino group of guanine. Representative hydrogen bond acceptors include the N3 of purines and the O2 of pyrimidines in dsDNA. Other preferred hydrogen bond donors and acceptors include amino acids, nucleosides, and carbohydrates.

Cyclic compounds according to the invention comprise at least one hydrogen bond donor or acceptor, and under physiological conditions form at least one hydrogen bond with a nucleotide present in a target nucleotide sequence in a double-stranded nucleic acid. Target nucleotide sequences comprise at least 4, and may comprise 5, 6, 7, 8, 9, 10, 11, 12, 13, 14, 15, 16, 17, 18, 19, 20, or more nucleotide base pairs. While it is desirable to form at least one hydrogen bond with at least one of the nucleotides of a Watson-Crick base pair in a double-stranded target nucleotide sequence, it is not essential.

As used herein, "subnanomolar affinity" means binding that is characterized by a dissociation constant, $K_d$, of less than 1 nM, as measured by DNase I footprint titration. Preferably, polyamides of the present invention are characterized by subnanomolar binding affinity for the identified target DNA sequence. As used herein, the "selectivity" of the binding of a polyamide to a DNA sequence is the ratio of the dissociation constant, $K_d$, as measured by DNase I footprint titration of binding the polyamide to a mismatch DNA sequence divided by the corresponding dissociation constant of the binding of the polyamide to the identified target DNA sequence. Preferably, polyamides of the present invention are characterized by a selectivity of about 5 or greater, more preferably a selectivity of greater that about 10.

A representative, but non-exhaustive list, of cyclic compounds within the scope of the instant invention includes cyclic polyamides and oligosaccharides. A number of such compounds, and their design and synthesis, are described herein.

B. Cyclic Polyamides

As used herein "polyamide" refers to a polymer of subunits chosen from the set below:

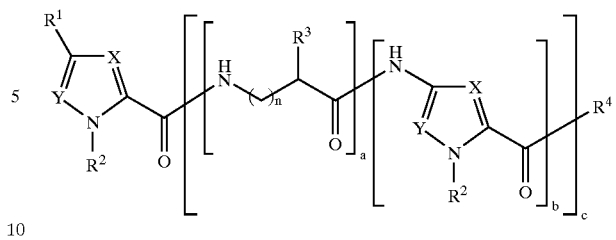

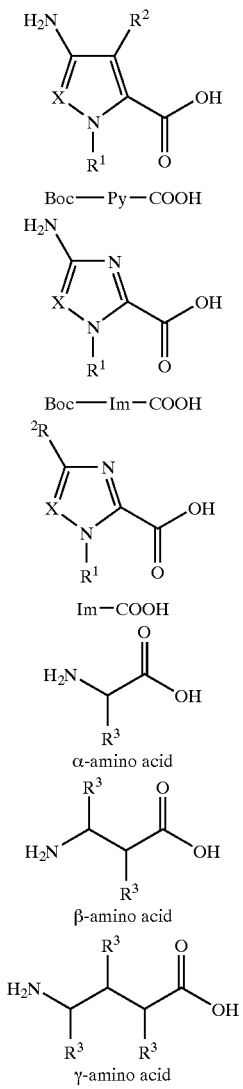

Boc—Py—COOH

Boc—Im—COOH

Im—COOH

α-amino acid

β-amino acid

γ-amino acid where $R^1$ is $C_{1-100}$ alkyl (preferably $C_{1-10}$ alkyl such as methyl, ethyl, isopropyl), $C_{1-100}$ alkylamine (preferably $C_{1-10}$ alkylamine such as ethylamine), $C_{1-100}$ alkyldiamine (preferably $C_{1-10}$ alkyldiamine such as N,N-dimethylpropylamine), a $C_{1-100}$ alkylcarboxylate (preferably a $C_{1-10}$ alkylcarboxylate such as $CH_2COOH$), $C_{1-100}$ alkenyl (preferably $C_{1-10}$ alkenyl such as $CH_2CH=CH_2$), or a $C_{1-100}$ alkynyl (preferably $C_{1-10}$ alkenyl such as $CH_2CH\equiv CH_3$), or a $C_{1-100}L$, where L groups can be independently chosen from biotin, oligodeoxynucleotide, N-ethylnitrosourea, fluorescein, bromoacetamide, iodoacetamide, DL-α-lipoic acid, acridine, ethyl red 4-(psoraen-8-yloxy)-butyrate, tartaric-acid, (+)-α-tocopheral.

where $R^2$ is chosen from H, $NH_2$, OH, SH, Cl, Br, F, N-acetyl, or N-formyl.

where $R^3$ is H, $NH_2$, OH, SH, Br, Cl, F, OMe, $CH_2OH$, $CH_2SH$, $CH_2NH_2$.

where X is chosen from N, CH, COH, $CCH_3$, $CNH_2$, CCl, CF.

More specifically, "polyamide" refers to a polymer of comprising one or more subunits of the formula (II), below where $R^1$ is chosen from H, $NH_2$, SH, Cl, Br, F, N-acetyl, or N-formyl.

where $R^2$ is $C_{1-100}$ alkyl (preferably $C_{1-10}$ alkyl such as methyl, ethyl, isopropyl), $C_{1-100}$ alkylamine (preferably $C_{1-10}$ alkylamine such as ethylamine), $C_{1-100}$ alkyldiamine (preferably $C_{1-10}$ alkyldiamine such as N,N-dimethylpropylamine), a $C_{1-100}$ alkylcarboxylate (preferably a $C_{1-10}$ alkylcarboxylate such as $CH_2COOH$), $C_{1-100}$ alkenyl (preferably $C_{1-10}$ alkenyl such as $CH_2CH=CH_2$), or a $C_{1-100}$ alkynyl (preferably $C_{1-10}$ alkynyl such as —$CH_2C\equiv CH_3$), or a $C_{1-100}L$, where L groups can be independently chose from biotin, oligodeoxynucleotide, N-ethylnitrosourea, fluorescein, bromoacetamide, iodoacetamide, DL-α-lipoic acid, acridine, ethyl red, 4-(psoraen-8-yloxy)-butyrate, tartaric acid, (+)-α-tocopheral.

where $R^3$ is chosen from H, $NH_2$, OH, SH, Br, Cl, F, Ome, $CH_2OH$, $CH_2SH$, $CH_2NH_2$.

where $R^4$ is —$NH(CH_2)_{0-100}NR^5R^6$ or $NH(CH_2)_m CO NH(CH_2)_{0-100} NR^5R^6$ or $NHR^5$ or $NH(CH_2)_m CONHR^5$. Where $R^5$ and $R^6$ are independently chosen from H, Cl, NO, N-acetyl, benzyl, $C_{1-100}$ alkyl, $C_{1-100}$ alkylamine, $C_{1-100}$ alkyldiamine, $C_{1-100}$ alkylcarboxylate, $C_{1-100}$ alkenyl, a $C_{1-100}$ alkynyl. Where m is an integer value ranging from 0 to 12.

where X and Y are chosen from the following, N, CH, COH, $CCH_3$, $CNH_2$, CCl, CF.

a is an integer chosen from values of 0 or 1 b is an integer chosen integer values ranging from 1 to 5.

c is an integer value ranging from 2 to 10.

Hereinafter, N-methylpyrrolecarboxamide may be referred to as "Py", N-methylimidazolecarboxamide may be referred to as "Im", γ-aminobutyric acid may be referred to as "γ", β-alanine may be referred to as "β", glycine may be referred to as "G", dimethylaminopropylamide may be referred to as "Dp", and ethylenediaminetetraacetic acid may be referred to as "EDTA".

C. Other Cyclic Compounds

In addition to cyclic polyamides, the present invention extends to other cyclic compounds that serve as molecular scaffolds comprised of units, some or all of which act hydrogen bond donors or acceptors, that provide an array of hydrogen bond donors and acceptors sufficient to enable specific and sensitive interaction with a particular sequence of nucleotides in a duplex nucleic acid molecule. Such compounds include arrays of nucleotides, carbohydrates, lipids, and other compounds known in the art.

D. Cyclic Compound Polymers

As those in the art will appreciate, certain embodiments of the present invention concern cyclic compound polymers comprised of two or more different compounds, at least one of which is a cyclic compound according to the invention. Representative examples of such compounds include conjugates between cyclic compounds and nucleic acids and/or proteins or polypeptides. In a cyclic acid-nucleic acid conjugate, the cyclic compound is covalently attached to the nucleic acid molecule. The nucleic acid is preferably a single-stranded oligonucleotide, although double-stranded nucleic acids can also be used. On the other hand, cyclic compound-polypeptide conjugates relate to those wherein the polypeptide and cycle are associated by any linkage, preferably one that is covalent.

E. Bi-Functional Cyclic Compounds

The design of bifunctional molecules target specific nucleotide sequences in double-stranded nucleic acid typically requires the integration of two separate entities: recognition and functional activity. Cyclic compounds that specifically bind with the desired affinity (e.g., subnanomolar affinity) to a predetermined, double-stranded nucleic acid sequence are linked (preferably covalently, but non-covalent, high affinity interactions between two members of a binding pair (e.g., streptavidin and biotin) to a functional molecule, providing a bifunctional conjugate. Such bifunctional molecules can be used in variety of contexts, including therapeutically, prophylactically, diagnostically, and in research (e.g., in DNA, particularly genomic DNA, sequencing).

Cyclic compounds according to this invention can be conjugated to a variety of functional molecules, which can be independently chosen from, but is not limited to, aryl-boronic acids, biotins, polyhistidines comprised from about 2 to 8 amino acids, haptens to which an antibody binds, solid phase supports, oligodeoxynucleotides, N-ethylnitrosourea, fluorescein, bromoacetamide, iodoacetamide, DL-α-lipoic acid, acridine, captothesin, pyrene, mitomycin, texas red, anthracene, anthrinilic acid, avidin, DAPI, isosulfan blue, malachite green, psoralen, ethyl red, 4-(psoraen-8-yloxy)-butyrate, tartaric acid, (+)-α-tocopheral, psoralen, EDTA, methidium, acridine, Ni(II)•Gly-Gly-His, TO, Dansyl, pyrene, N-bromoacetamide, and gold particles. Such bifunctional compounds are useful for dsDNA affinity capture, covalent dsDNA modification, oxidative dsDNA cleavage, and dsDNA photocleavage, among other applications. Such bifunctional compounds are also useful for dsDNA detection by providing a cyclic compound linked to a detectable label. Detailed instructions for synthesis of such bifunctional polyamides can be found in copending U.S. provisional patent application No. 60/043,444.

An additional representative class of bifunctional cyclic compounds according to the invention are cyclic polyamides which bind in the minor groove of dsDNA but to which is attached a group that intereacts, directly or indirectly, with cellular components (e.g., a DNA binding protein such as a transcription factor, a polymerase, etc.) that interact with the neighboring major groove of the dsDNA. An example of such an indirect interaction includes altering the charge (e.g., neutralization) of a portion of the phosphate backbone of one or both strands of a dsDNA such that the resulting electrostatic change(s) in the particular DNA microenvironment is sufficient to disrupt the interaction of a cellular component that interacts the affected portion of the major groove. A hairpin polyamide that incorporated a three amino acid group neutralized the regional charge on the adjacent DNA backbone and disrupted binding of a DNA binding protein that interacted with the adjacent major groove.

II. Cyclic Compound Design

Cyclic compounds of the invention can be designed rationally, which design will preferably take into consideration at least the sequence of nucleotide base pairs of the target sequence. However, in certain embodiments of the invention, such information is not required or may not be available.

Notwithstanding the foregoing, it is expected that in most situations the sequence of nucleotide base pairs of the target sequence will be known. With such information, the design of certain cyclic compounds can be undertaken. For example, for polyamides, a series of simple pairing rules have been established for designing sequence-specific polyamides, which rules are described below.

Preferred specific symmetrical cyclic polyamides according hereto are in the form of two polymer portions covalently linked by linkers (although cycle formation by direct covalent attachment of one polymer portion to another at two locations, as well as one such direct linkage between the two polymers and at least one indirect linkage via a linker, is also within the scope hereof), wherein the two polymer portions comprise the following structures:

Polymer 1:

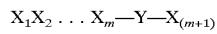

$X_1X_2 \ldots X_m-Y-X_{(m+1)}$

Polymer 2:

$X_{(2m-1)}X_{2m}$ wherein $X_1$, $X_2$, $X_m$, $X_{(m+1)}$, $X_{(2m-1)}$, and $X_{2m}$ are carboxamide residues forming carboxamide binding pairs (i.e., hydrogen bond donor/donor or donor/acceptor pairs) $X_1/X_{2m}$, $X_2/X_{(2m-1)}$, $X_m/X_{(m+1)}$, and Y is β-alanine or another aliphatic register restoring moiety, and where carboxamide binding pair $X_1/X_{2m}$ corresponds to base pair $N_1 \cdot N'_1$, carboxamide binding pair $X_2/X_{(2m-1)}$ corresponds to base pair $N_2 \cdot N'_2$, and carboxamide binding pair $X_m/X_{(m+1)}$ corresponds to base pair $N_m \cdot N'_m$. It is also understood that, for purposes of these embodiments, m shall be greater than or equal to 2, and that the second polymer may also comprise register-restoring moiety, if necessary.

In general, the specific cyclic polyamides were designed by using a method that comprises the steps of identifying the target DNA sequence 5'-$WN_1N_2 \ldots N_mW$-3'; representing the identified sequence as 5'-Wab . . . xW-3', wherein a is a first nucleotide to be bound by the $X_1$ unit, b is a second nucleotide to be bound by the $X_2$ unit, and x is the corresponding nucleotide to be bound by the $X_m$ unit; defining a as A, G, C, or T to correspond to the first nucleotide to be bound by a carboxamide residue in the identified six base pair sequence.

Units for the polymers of these cyclic polyamides were selected sequentially as follows: Im was selected as the $X_1$ unit and Py as the $X_{2m}$ unit if a was G. Py was selected as the $X_1$ unit and Im a the $X_{2m}$ unit if a was C. Hp was selected as the $X_1$ unit and Py as the $X_{2m}$ unit if a was T. Py was selected as the $X_1$ unit and Hp as the $X_{2m}$ unit if a was A.

The remaining units were selected in the same fashion. Im was selected as the $X_2$ unit and Py was the $X_{2m-1}$ unit if b was G. Py was selected as the $X_2$ unit and Im as the $X_{2m-1}$ unit if b was C. Hp was selected as the $X_2$ unit and Py as the $X_{2m-1}$ unit if b was T. Py was selected as the $X_2$ unit and Hp as the $X_{2m-1}$ unit if b was A.

The selection of units was continued through m iterations. In the last iteration, Im was selected as the $X_m$ unit and Py was the $X_{m+1}$ unit if x was G. Py was selected as the $X_m$ unit and Im as the $X_{m+1}$ unit if x was C. Hp was selected as the $X_m$ unit and Py as the $X_{m+1}$ unit if x was T. Py was selected as the $X_m$ unit and Hp as the $X_{m+1}$ unit if x was A.

In one preferred embodiment, the cyclic polyamide includes at least four consecutive unit pairs, wherein each unit pair comprises a carboxamide pair for binding to at least four base pairs in a dsDNA. In another preferred embodiment, the cyclic polyamide includes at least five consecutive unit pairs, wherein each unit pair comprises a pair for binding to at least five base pairs in a dsDNA. In yet another preferred embodiment, the cyclic polyamide includes at least six consecutive unit pairs, wherein each unit pair comprises a carboxamide pair for binding to at least six base pairs in a dsDNA. In one preferred embodiment, the cyclic polyamides have four unit pairs, wherein each unit pair comprises a carboxamide binding pair, that will distinguish A•T, T•A, C•G, and G•C base pairs in the minor groove of a dsDNA.

For preferred cyclic polyamides, DNA target sequence recognition thus depends on a code of unit pairings in the minor groove of double stranded DNA. Notwithstanding the foregoing, in many symmetric cyclic polyamides according to the invention, it will be preferred to incorporate one or more aliphatic, register restoring moieties as a unit intone or both polymer portions. This is particularly true when design considerations indicate that two or more Im residues should be placed in the same polymer portion, especially when Im residues are adjacent. Similarly, molecular modeling can be used to predict when and where to include such register-restoring moieties when other units are incorporated into such compounds. Moreover, inclusion of such moieties, particularly those that do not participate in hydrogen bond formation between the cyclic compound and a double-stranded nucleic acid, in cyclic compounds according to the invention will provide additional structural flexibility. Such structural flexibility will enable a better three-dimensional "fit" between a cyclic compound and its target sequence, thereby enhancing either or both binding affinity and specificity.

While pairing rules exist for polyamides, including cyclic polyamides, such may not be the case for other cyclic compounds within the scope hereof. In such situations, other approaches to compound design may be undertaken. Such approaches range from random synthesis methods to the use of molecular modeling. For example, molecular modeling based on new or existing high resolution X-ray crystallographic and/or NMR data can be used to predict the spatial arrangement of hydrogen bond donors and acceptors in a target nucleotide sequence. This information can then be used to design a cyclic compound, or preferably a library of cyclic compounds, which structurally produces a three dimensional molecular scaffold of hydrogen bond acceptors and donors capable of forming a sufficient number of hydrogen bonds with the target nucleotide sequence under physiological conditions to allow the desired compound/target interactions to occur.

III. Cyclic Compound Synthesis

Any suitable method can be employed to synthesize cyclic compounds according to the invention. Such methods include those performed in solution and those performed on a solid support. The latter method is particularly preferred when synthesizing relatively small quantities (e.g., less than one gram) of a plurality of cyclic compounds, as may occur in the production of a library of cyclic compounds for screening against one or more target sequences. Moreover, solid phase methods may be adapted to machine-assisted protocols, thereby enabling automated or semi-automated methods to be carried out.

Representative embodiments of such methods relate to the solid phase synthesis of cyclic polyamides comprising seven or more units. For purposes of this illustrative description, all units are amino acids. However, this need not be so in each of these embodiments. Such embodiments are derived by modification of in situ neutralization methods described by Kent and coworkers (Schnolzer, et al., *Int. J. Peptide Protein Res.*, vol. 40:180–193 (1992); Milton, et al., *Science*, vol. 252:1445–48 (1992)), and can be performed as described in U.S. Ser. No. 08/607,078.

To summarize, such methods preferably begin by obtaining or preparing a suitable solid support, for example, a polystyrene resin. Suitable supports include Boc-Py-PAM/BAM resins, Boc-Py-G-PAM/Boc-Py-β-PAM resins, and the corresponding Boc-Im resins. Preferably, the resin will contain a linker, and optionally a spacer, molecule that enables facile attachment and removal of the desired polyamide. If necessary for subsequent manipulations, the resin is then deprotected, for example, by washing it with dichloromethane followed by Boc group removal using 65% trifluoroacetic acid (TFA)/35% dichloromethane/0.5 M thiophenol for 20 min., followed by washing first with dichloromethane and then with dimethylformamide (DMF).

A protected and activated carboxy terminal amino acid (wherein the amino group is protected and the carboxylic group is activated, e.g., Boc-Py, Boc-Im-OBt, Fmoc-Py-Obt, Fmoc-Im-Obt, and particularly a Boc-protected allyl ester-Py monomer), or an intermediate amino acid polymer (e.g., an amino acid dimer or trimer), is then reacted with the activated amino functionality of the resin. Diisopropylethylamine is preferably present during the coupling reaction. The use of high concentrations of amino acids is preferred to enhance coupling reaction rates. After approximately 45 min., the resin is washed with DMF. When coupling amino-protected Py to the amino functionality of Im, it is preferable to use a Py monomer activated as a symmetric anhydride rather than an -OBt ester, using the protocol described by Ding, et al., *Acta Chem. Scand.*, vol. 23:751 (1963), as modified in U.S. Ser. No. 08/607,078.

Assembly of the polyamide is continued by the sequential addition of the remaining amino acids. After coupling of the final amino acid to the nascent polyamide, the amino group is deprotected. When an allyl group is present, it can be removed by a palladium catalyst. The polyamide can then be released from the resin by any suitable chemistry, e.g., by treatment with dimethylaminopropylamine. A cycle can then be formed by treatment with diphenylphophoryl azide (DPPA)in dilute DMF. See U.S. Ser. No. 08/607,078 for a detailed discussion of such methods and variations thereon.

Cyclic polyamides made in accordance herewith are preferably purified prior to use. RP-HPLC is a particularly preferred purification method. Irrespective of the purification method employed, purity levels exceeding about 90%, preferably above about 95%, and even more preferably above about 99%, are desirable.

IV. Screening Methods

Another aspect of the present invention concerns methods of screening compounds made in accordance herewith to identify one or more cyclic compounds capable of binding to a selected target nucleotide sequence in a double-stranded nucleic acid (the screening substrate), particularly duplex DNA. Such methods involve combining one or more test compounds to be screened, or a mixture containing the test compound(s), in an appropriate assay system. Typically, the assay system employs a double-stranded nucleic acid containing one or more test sequences, i.e., the nucleotide sequence(s) with which one or more of the test compound(s) will hopefully interact, and one or more other substances (e.g., nucleic acids, polypeptides, small molecules, polysaccharides, etc.) each of which interacts with the same or a different specific nucleotide sequence in duplex nucleic acid molecules, i.e., the control sequence, which control sequence(s) are also present in the assay mixture. Moreover, as those in the art will appreciate, the test and control sequences can be the same, partially the same (e.g., overlapping by one or more base pairs), or different. When different, they may be separated by one or more base pairs, but are preferably juxtaposed, i.e., not overlapping and not separated by any nucleotide base pairs. Indeed, the test and control sequences can be present on different screening substrates.

Suitable test systems typically include a duplex nucleic acid molecule (preferably dsDNA) containing at least one test sequence, and preferably at least one control sequence. In those instances when a screening substrate comprises only a test sequence, and does not contain a screening sequence, or vice versa, the assay will also, contain a second screening substrate containing the test or control sequence not found on the first screening substrate. The screening substrate(s) may contain one or more copies of the test and/or screening sequences.

The test sequence(s) can be obtained in a number of ways. For example, such sequences can be randomly generated (for example, by automated oligonucleotide synthesis) for a shotgun approach. Alternatively, one or more specific sequences (e.g., a specific promoter implicated in the manifestation of a particular disease) may be incorporated into the screening substrate.

Preferred control sequences for use in such assays include regulatory regions of disease-associated genes (e.g., genes implicated in cancer or autoimmune disease) and of genes of pathogens (e.g., viruses and eukaryotic and prokaryotic pathogens). In such instances, the binding substances employed will preferably be the proteins (or DNA binding domains thereof) known or suspected to interact with such sequences in vivo. Alternatively, the control sequence/binding substance used may be part of a well characterized protein/nucleic acid system, for example, the lac operator and repressor of $E.$ $coli$ or the $o_L$-$o_R$/cro repressor of phage lambda. Indeed, essentially any well characterized duplex nucleic acid/corresponding binding substance interaction can be readily adapted to the instant methods.

In preferred embodiments, the duplex nucleic acid-binding substance used in the assay system comprises a DNA binding protein (or portion thereof that interacts with dsDNA) that binds with high affinity (preferably with subnanomolar affinity to a control sequence, e.g., the polypeptide's cognate binding site, in a manner that is preferably substantially independent of the sequences overlapping with or adjacent or juxtaposed to the control sequence. However, the polypeptide (or other duplex nucleic acid-binding substance) should be sensitive to high affinity binding (which, with respect to this aspect of the invention, means a substance with a $K_a$ of less than about 100 nM, preferably less than about 10 nM, particularly less than about 1 nM) of a compound to a test sequence, especially when the test sequence is the same as, overlapping with, or juxtaposed to (including being located on a separate screening substrate molecule) the control sequence.

To function properly, the duplex nucleic acid binding substance should be present in an amount that saturates the control sequence(s). For each assay, the test molecule is incubated in an assay mixture also containing the screening substrate(s) and binding substances for a period of time sufficient to permit equilibrium binding to be established between the test molecule(s), binding substance(s), and test and control sequences. The conditions under which such assays are performed are preferably in vitro conditions, although the instant methods can readily be adapted for application in cultured cells. Indeed, in preferred methods, test compounds identified in an in vitro assay as having the desired activity (e.g., subnanomolar binding affinity and the ability to substantially prevent, inhibit, or otherwise disrupt the interaction of a binding substance with its particular binding site on a screening substrate) are then subjected to screening in cultured cells to confirm their inhibitory activity on binding substance/duplex nucleic acid interactions. Those compounds exhibiting the desired activity profile are then typically for further studies, including those conducted in vivo.

Typically, in performing such screening assays the amount of binding substance bound to the control sequence of the screening substrate is compared before and after the addition of the test molecule or mixture. In preferred embodiments, comparison of a binding substance-bound to free dsDNA can be accomplished using a gel band-shift assay, filter-binding assay, or a capture/detection assay. Alternatively, indirect detection can be also be performed, for example, by comparing the activity of a restriction enzyme's cleavage of its cognate restriction site in the presence or absence of the test compound, or by examining the level of expression of a reporter gene (as may be detected at the nucleic acid or protein level, or by detection of some other signal, e.g., the amount of light generated by an assay system in which the gene, the expression of which is to be modulated, is luciferase.

Thus, screening methods according to the invention include those in which binding substance/duplex nucleic acid interactions are directly assayed (e.g., a gel shift assay), as well as those involving more indirect methods, e.g., detection of reporter gene expression. The methods of the invention may also be carried out on one or few test compounds or, alternatively, be performed on a high throughput basis, wherein 100–10,000 or more test compounds are screened against one or more test sequences. Such high throughput methods are particularly useful in conjunction with the solid state cyclic polyamide synthesis methods described herein.

V. Compositions

The compounds described herein can be administered to cells in vitro or in vivo. In addition, compounds according to the invention can also be used in cell-free environments, for example, in experiments wherein cell extracts containing a fraction which contains double-stranded nucleic acid (e.g., a fraction containing nuclei, nuclear DNA, mitochondria, or miotochondrial DNA) or in, experiments using dsDNA (e.g., duplexed oligonucleotides substantially complementary over at least a portion of their lengths, restriction fragments, plasmids, etc.). Thus, the intended application for a cyclic compound according to the invention will typically dictate the ultimate product composition, as those in the art will appreciate.

For example, wherein a cyclic compound according to the invention (e.g., a cyclic polyamide) is to be used therapeutically (e.g., as an animal, particularly a human, medicine), it is formulated into an appropriate therapeutic composition. Similarly, if the compound is to be used in a diagnostic application, it will be incorporated into an appropriate composition for such application.

In its most simple form, a composition according to the invention may simply comprise a cyclic compound according to the invention, preferably as a salt. More typically, however, a composition according to the invention will comprise a cyclic compound and one or more other compounds. Such other compounds, or excipients, may or may not have independent or activity.

The term "pharmaceutically acceptable" or "pharmaceutical" as used herein refers to solutions or components of the pharmaceutical composition that do not prevent the therapeutic compound from exerting a therapeutic effect and do not cause unacceptable adverse side effects. For purposes of brevity, when used herein "pharmaceutical" shall be understood to include both human and other animal (e.g., domestic and other animal species, particularly those of agricultural importance) application. Examples of pharmaceutically acceptable reagents are provided in *The United States Pharmacopeia The National Formulary*, United States Pharmacopeial Convention, Inc., Rockvlille, Md. 1990 and *FDA Inactive Ingredient Guide* 1990, 1996 issued by the Division of Drug Information Resources (both are hereby incorporated by reference herein, including any drawings). Unacceptable side effects vary for different diseases or conditions to be treated or prevented. Generally, the severity of the disorder being treated, will dictate the severity of the toxic effects that will be tolerated. Unacceptable side effects for different diseases are known in the art.

The term "physiologically acceptable" defines a carrier, diluent, or excipient that does not cause significant irritation to an organism and preferably does not abrogate the biological activity and properties of the compound or other active ingredients, if any.

The term "carrier" defines a chemical compound that facilitates the incorporation of a compound into cells or tissues. For example dimethyl sulfoxide (DMSO) is a commonly utilized carrier as it facilitates the uptake of many organic compounds into the cell's or tissues of an organism.

The term "diluent" defines chemical compounds diluted in water (or another solvent) that will dissolve the compound (s) of interest as well as stabilize the biologically active form of the compound(s) and other active ingredient(s), if present. Many salts dissolved in buffered solutions are utilized as diluents in the art. One commonly used buffered solution is phosphate buffered saline because it mimics the salt conditions of human blood. Because buffer salts can control the pH of a solution at low concentrations, a diluent rarely modifies the biological activity of a compound having biological activity, e.g., a cyclic compound according to the invention.

The term "solvent" as used herein refers to a chemical that facilitates solubilization of a compounds according to the invention. Examples of solvents include, but are not limited to, pharmaceutically acceptable alcohols, such as ethanol, benzyl alcohol, and glycerol; polyoxyhydrocarbyl compounds (e.g., a water soluble carbohydrate such as glucose, sucrose, maltotriose, and the like; a water soluble carbohydrate derivative such as gluconic acid and mannitol, oligosaccharides; and water soluble polymers such as polyvinylpyrrolidone, polyvinyl alcohol, polyethers such as polyoxyalkylenes, including polyethylene glycol (PEG) and derivatives thereof, or other water soluble mixed oxyalkylene polymers and the polymeric form of ethylene glycol), pharmaceutically acceptable surfactants, and pharmaceutically acceptable oils.

The term "pharmaceutically acceptable surfactant" as used herein refers to a compound that can solubilize compounds of the invention into aqueous solutions, if necessary. Preferably for parenteral formulations, the surfactant is a non-ionic surfactant. A "pharmaceutically acceptable oil" is an oil such as mineral oil or vegetable oil and the like.

A. Formulation.

For example, when a cyclic compound according to the invention is to be used to treat a human disease or disorder, it will typically be human patient per se, or in pharmaceutical compositions where they are mixed with other active ingredients, as in combination therapy, and/or one or more suitable carriers, excipient(s) (i.e., a more or less inert substance added to a composition to confer a suitable consistency or to enable a drug to be formed), adjuvants, stabilizers, and vehicles. The composition may be in solid, liquid, gel, or aerosol form. Techniques for formulation of the cyclic compounds of the instant application may be found in "Remington's Pharmaceutical Sciences," Mack Publishing Co., Easton, Pa. (1995)

The pharmaceutical compositions of the present invention may be manufactured in a manner that is itself known, e.g., by means of conventional mixing, dissolving, granulating, dragee-making, levigating, emulsifying, encapsulating, entrapping, spray drying, or lyophilizing processes.

Proper formulation is dependent upon the route of administration chosen. For injection, the agents of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compound(s) with pharmaceutically acceptable carriers, excipients, etc. well known in the art. Such carriers excipients, etc. enable the compounds of the invention to be formulated as tablets, pills, dragees, capsules, liquids, gels, syrups, slurries, suspensions, and the like. Pharmaceutical preparations for oral use can be obtained by adding a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. In certain non-human applications, such compositions may be included in food preparations.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the cyclic compounds for use according to the present invention are conveniently delivered in the form of powder, or more preferably, as an aerosol spray from a pressurized pack, nebulizer, or metered dose inhaler, with the use of a suitable propellant, e.g., dichlorodifluoromethane, trichlorofluoromethane, dichlorotetrafluoroethane, carbon dioxide, or other suitable gas.

Cyclic compounds can also be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions, emulsions in oily or aqueous vehicles, and lyophilized powders for reconstitution in an appropriate solution (e.g., sterile pyrogen-free water) prior to use, and may contain formulatory agents such as suspending, stabilizing, and/or dispersing agents.

In particular, pharmaceutical formulations for parenteral administration include aqueous solutions of the active compounds in water-soluble form. Additionally, suspensions of the active compounds may be prepared as appropriate oily injection suspensions. Aqueous injection suspensions may contain substances that increase the viscosity, of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

In addition to the formulations described previously, the cyclic compounds of the invention may also be formulated as a depot preparation. Such long acting formulations may be administered by implantation (for example, subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Other delivery systems for the pharmaceutical compositions compounds may also be employed. For example, liposomes and emulsions are well known examples of delivery vehicles or carriers for hydrophobic drugs. Use of delivery vehicles such as liposomes affords the opportunity to provide one or more targeting moieties in the composition, thereby enabling the cyclic compound to be delivered to a particular cell or tissue. Cell and tissue targeting techniques and moieties are known in the art, and will vary depending upon the particular application.

Additionally, cyclic compounds may be delivered using a sustained-release system, such as semi-permeable matrices of solid hydrophobic polymers containing the therapeutic agent. Various types of sustained release materials have been established and are well known by those skilled in the art. Sustained-release capsules may, depending on their chemical nature, release the compounds for a few weeks up to over 100 days. Depending on the chemical nature and the biological stability of the cyclic compound, additional strategies for protein stabilization may be employed.

For non-animal application, for example, to plants, the compositions of the invention will typically comprise the cyclic compound in a solution which can be sprayed on the plants or included in irrigation water. Alternatively, solid dosage forms that can be broadcast upon or near the targeted plant (or seeds) can also be prepared in accordance with methods known in the art.

Many of the cyclic compounds of the invention may be provided as salts with pharmaceutically compatible counterions. Pharmaceutically compatible salts may be formed with many acids, including, but not limited to, hydrochloric, sulfuric, acetic, lactic, tartaric, malic, succinic, etc. acid. Salts tend to be more soluble in aqueous or other protonic solvents than are the corresponding free base forms.

B. Administration

In a therapeutic or prophylactic context, the term "administering" relates to a method of incorporating or delivering a cyclic compound of the invention into cells or tissues of an organism, be it an animal or a plant. As those in the art will appreciate, depending upon application, administration can be either in vivo (i.e., to a living animal or plant) or in vitro (e.g., to cultured cells). With regard to in vivo administration to an animal (e.g., a human), many administration techniques exist, including, but not limited to, oral, parenteral (e.g. intravenous, intramuscular, subcutaneous, intraperitoneal, and intraarticular injection), and aerosol administration. The compounds may also be administered in a depot or sustained release formulation. For in vitro (including ex vivo), therapy, multiple administration techniques also exist, including cell microinjection techniques, simple diffusion, and carrier techniques.

To affect gene expression in a cell, which may include causing an increase or a decrease in the expression of one or more genes, an effective quantity of one or more cyclic compounds polyamide is delivered to and internalized by the cell, be it in vivo or in vitro. Effective extracellular concentrations of polyamides that can modulate gene expression range from about 0.01 nanomolar (nM) to about 1 micromolar ($\mu$M), more preferably from about 1 nM to about 0.1 $\mu$M, particularly from about 1 nM to about 0.05 $\mu$M, especially about 10 nM to about 0.75 $\mu$M. Gottesfeld, et al., *Nature,* vol. 387:202–205 (1997).

Notwithstanding the foregoing, those in the art will appreciate that, with regard to therapeutic or prophylactic treatment, the selection of the precise concentration, composition, and delivery regimen will be influenced by, inter alia, the specific pharmacological properties of the particular composition, the intended use, the nature and severity of the condition being treated or prevented, the age, weight, gender, and physical condition of the intended recipient, as well as the route of administration. Such considerations are within the purview of the skilled artisan. For example, to determine effective amounts and concentrations of cyclic polyamides in vitro, a suitable number of cells is plated on tissue culture plates and various quantities of one or more cyclic polyamides are added to separate wells. Expression of the particular gene(s) whose expression is(are) to be modulated following exposure to the compound can be monitored in the cells or medium by detecting the amount of the protein gene product present as determined by various techniques utilizing specific antibodies, including ELISA and Western blotting. Alternatively, gene expression following exposure to a polyamide can be monitored by detecting the amount of messenger RNA present, as determined by various techniques, including Northern blotting and RT-PCR.

Similarly, to determine effective amounts and concentrations of cyclic compounds for in vivo administration, a sample of body tissue or fluid, such as plasma, blood, urine, cerebrospinal fluid, saliva, or biopsy of skin, muscle, liver, brain or other appropriate tissue source, can be analyzed. Gene expression following exposure to a polyamide can be monitored by detecting the amount of the protein gene product present as determined by various techniques utilizing specific antibodies, including ELISA and Western blotting. Alternatively, gene expression following exposure to the compound can be monitored by the detecting the amount of messenger RNA present as determined by various techniques, including northern blot and RT-PCR. Such determinations can also be made by these and others techniques applied to cells from an organism of the type to be treated (or an animal model therefore) before and after administration of a composition according to the invention. These and other strategies known in the art can be readily adapted to a given application for a particular cyclic compound.

VI. Applications

A. Modulation of Gene Expression

The cyclic compounds described herein are useful for modulating expression of one or more genes in vitro or in vivo. Such modulation is typically accomplished by delivering a quantity of a cyclic compound according to the invention sufficient to interact with a specific nucleotide sequence present in double-stranded nucleic acid (e.g., dsDNA), preferably a regulatory sequence, and cause a change in expression of a gene functionally associated with such regulatory sequence. Such sequences include promoters, enhancers, repressor binding sites, and any other nucleotide sequence targeted by a DNA binding protein or other substance in a cell that can affect transcription. Cellular events involved in transcription include nucleosome formation and dissociation, formation of RNA transcription complexes, transcription initiation, etc.

Genes the expression of which can be modulated in accordance with this invention include cellular or viral genes. Such cellular genes include both eukaryotic and prokaryotic genes. The cellular gene(s) can be present in original, native cells, in cells transfected or transformed with a recombinant DNA construct comprising the cellular gene, or in an in vitro, cell-free system, for example, as a reporter gene. Similarly, a viral gene can be present in a cell or in an in vitro, cell-free system.

The polyamides of the present invention can act as specific inhibitors or activators of gene transcription in vivo or in vitro as therapeutic or prophylactic agents in treating disease conditions related to the transcription of at least one cellular or viral gene.

Certain embodiments of the present invention concern the use of a unique or rare sequence adjacent to or overlapping with the binding sites for common transcription factors as the target sequences for the design of cyclic compounds. It has been found that sequences adjacent to the binding sites for required transcription factors are unique, i.e., are not associated with genes in the current publicly available nucleic acid databases.

Many protein coding genes utilize both gene- and tissue-specific transcription factors as well as general transcription factors for transcription of mRNA by RNA polymerase II. The binding sites for these protein factors are found in numerous genes, whereas the sequences adjacent to or overlapping with these binding sites tend to be unique for each gene. Cyclic compounds can be designed which target sequences adjacent to or overlapping with the binding sites for these transcription factors, as well as to the binding sequences for these factors. Cyclic compounds that target these sequences will interfere with the binding of the protein factors to DNA and thereby inhibit transcription by RNA Polymerase II.

In other embodiments, cyclic compounds can be designed and synthesized that recognize and bind the sequences immediately adjacent to, or overlapping with, the site at which the minor groove-binding protein TATA-box binding protein (TBB) binds to TATA DNA can be designed. DNA sequences adjacent to or overlapping with TATA elements are gene-specific, whereas TATA elements are found in many protein-coding genes. For example, a hairpin polyamide bound to a sequence adjacent to the HIV-1 TATA element has been shown to inhibit HIV-1 promoter-specific transcription by RNA polymerase II. A cyclic compound designed to selectively bind this site would be useful to treating diseases associated with HIV-1 infection.

In other embodiments, the cyclic compounds will recognize and bind to an identified target sequence adjacent to the transcription factor protein binding site of a cellular gene, for example, a constitutively expressed gene under basal transcription control (e.g., the gene encoding the 5S ribosomal subunit).

In yet other preferred embodiments, the minor groove transcription factor protein of the cellular gene is TBP. Such preferred cellular genes include oncogenes such as LEF-1, Ets-1 and her-2/neu. Other such preferred cellular genes include genes encoding cytokines such as interleukins, including IL-2, IL-5 and IL-13, tumor necrosis factors, including TNF-alpha and TNF-beta, growth factors, including TGF-beta, and colony stimulating factors, including GM-CSF.

Using the above described rules, a sequence-specific cyclic compound can be designed that selectively binds to an identified target site adjacent to the binding site of a DNA binding protein, e.g., transcription factor. As used herein, "adjacent" includes cyclic compound binding sites wherein an end nucleotide base pair of the binding site is immediately contiguous to an end nucleotide of the DNA binding protein binding site, and cyclic compound binding sites separated from the protein binding site by from one to about 20, preferably from 1 to about 10 or fewer intervening nucleotide base pairs. The binding affinity of such a designed cyclic compound should be greater than the binding affinity of the native transcriptional element in order to inhibit transcription. The binding affinity can be ascertained by competitive inhibition experiments against a native transcription factor. "Overlapping" refers to a cyclic compound binding site wherein one to five nucleotide base pairs of the compound's binding site are shared with the binding site of the DNA binding protein.

A "promoter" is a regulatory sequence of dsDNA involved in the binding of RNA polymerase to initiate transcription of a gene. A "gene" is a segment of DNA which codes for a "gene product", typically a peptide, polypeptide, or protein, including the coding region, non-coding regions preceding ("leader") and following ("trailer") the coding region, as well as intervening non-coding sequences ("introns") between individual coding segments ("exons"). Coding refers to the representation of amino acids, start and stop signals in a three base "triplet" code, and other signals, such as polyadenylation signals. "Gene products" also include RNA molecules, for example, tRNAs, small nuclear RNAs, ribosomal RNAs, and catalytic RNAs (e.g., ribozymes). A "gene of interest refers" to a gene the expression of which is desired to be modulated using a cyclic compound according to the invention.

Promoters are often upstream ("'5 to") the transcription initiation site of the corresponding gene. Other regulatory sequences of DNA in addition to promoters are known, including sequences involved with the binding of transcription factors, including response elements that are the DNA sequences bound by inducible factors. "Enhancers" comprise yet another group of regulatory sequences of DNA that can increase the utilization of promoters, and can function in either orientation (5'→3' or 3'→5') and in any location (upstream or downstream) relative to the promoter. In some embodiments, the regulatory sequence has a positive activity, i.e., binding of an endogeneous ligand (e.g., a transcription factor) to the regulatory sequence increases transcription, thereby resulting in increased expression of the corresponding target gene. In such a case, interference with transcription by binding a polyamide to a regulatory sequence would reduce or abolish expression of a gene.

A promoter can also include or be adjacent to a regulatory sequence known in the art as a "silencer". A silencer generally has a negative regulatory effect on expression of the gene. In such cases, expression of a gene may be increased (also referred to as gene "activation" or "derepression") directly by using a cyclic compound according to the invention, e.g., a polyamide, to prevent binding of a factor to a silencer regulatory sequence, or indirectly by using such a compound to block transcription of a factor that interacts with a silencer.

To affect gene expression in a cell, which may include causing an increase or a decrease in gene expression, a quantity of one or more cyclic compounds effective to modulate transcription is contacted with the cell and internalized by the cell. The cell may be contacted by the polyamide in vivo or in vitro. Effective transcription inhibiting extracellular concentrations of polyamides that can module gene expression range from about 10 nanomolar to about 1 micromolar. Gottesfeld, J. M., et al., *Nature* 387:202–205 (1997). To determine effective amounts and concentrations of polyamides in vitro, a suitable number of cells is plated on tissue culture plates and various quantities of one or more polyamides are added to separate wells. Gene expression following exposure to a cyclic compound can be monitored in the cells or in the medium by detecting the amount of the protein gene product present as determined by various techniques utilizing specific antibodies, including ELISA and Western blot. Alternatively, gene expression following exposure to a cyclic compound can be monitored by detecting the amount of messenger RNA present as determined by various techniques, including Northern blot and RT-PCR.

Similarly, to determine effective amounts and concentrations of polyamides for in vivo administration, a sample of body tissue or fluid, such as plasma, blood, urine, cerebrospinal fluid, saliva, or biopsy of skin, muscle, liver, brain or other appropriate tissue source is analyzed. Gene expression following exposure to a cyclic compound can be monitored by detecting the amount of the protein gene product present as determined by various techniques utilizing specific antibodies, including ELISA and Western blot. Alternatively, gene expression following exposure to a cyclic compound can be monitored by detecting the amount of messenger RNA present as determined by various techniques, including Northern blot and RT-PCR.

1. Inhibition

The present invention provides cyclic compounds, including cyclic polyamides, which inhibit the transcription of DNA upstream or downstream of transcriptional factors such as the 5S RNA gene transcriptional factor TFIIIA, the minor groove-binding protein TATA-box binding protein (TBP) Ets-1, and LEF-1. Such compounds can act as gene-specific inhibitors of transcription since they are selective for the sequences flanking these protein binding sites that are, in turn, gene-specific.

2. Activation

In addition to being useful to inhibit gene transcription, the cyclic compounds according to the invention can also be used to activate transcription of one or more genes. Such activation will typically involve interference with, or inhibition of, binding of a repressor protein or a similar molecule to a specific regulatory region of the gene of interest. Accordingly, the methods used to design and synthesize cyclic compounds, particularly cyclic polyamides, to inhibit gene transcription can similarly be applied in the context of activation of a gene of interest.

B. Treatment/Prophylaxis

As will be clear to those in the art, the cyclic compounds described herein can be used to treat or prevent a variety of diseases and other conditions associated with the expression of one or more genes, and will thus have many applications, including anti-viral, anti-bacterial, anti-fungal, and anti-cancer applications.

In the treatment context, an appropriate amount of a cyclic compound according to the invention will be administered to an organism known to have, or suspected of having, a particular disease or disorder. In addition, cyclic compounds can be used prophylactically to prevent the development of an unwanted disease or disorder by preventing undesirable gene expression. In either context, the cyclic compounds will be administered in accordance with the teachings provided herein.

A representative example of how cyclic compounds according to the invention can be used in a therapeutic context concerns HIV. A recent review summarizes current knowledge of the protein factors required for the control of RNA initiation and elongation by RNA polymerase II at the HIV-1 promoter (Jones, K. A. and B. M. Peterlin. 1994. Control of RNA initiation and elongation at the HIV-1 promoter. *Annu. Rev. Biochem.*, 63:717–743). For HIV, the template for synthesis of both new viral RNA and messenger RNA (for viral protein synthesis) is the integrated provirus. HIV-1 utilizes the transcription machinery of the host cell but encodes its own trans-activators, Tat and Rev, that are responsible for RNA elongation and utilization.

The HIV-1 promoter is located in the U3 region of the leftward (5') long terminal repeat. The core promoter and enhancer elements span a region of approximately 250 base pairs and include TTA and initiator elements ad the binding sites for the following cellular transcription factors: Sp1, NF-κB, LEF-1, Ets-1 and USF. Sequences upstream of the NF-κB sites contribute only marginally to HIV-1 promoter activity enter in vitro or in transfected cell lymphoid cell lines. Waterman, M. L. and K. A. Jones, *New Biologist*, 2:621–636 (1990). However, these upstream sequences, and presumably the protein factors which bind these upstream sequences, are important for viral replication, and hence promoter activity, in peripheral blood lymphocytes and in some T cell lines. Kim, J., et al., *J. Virol*, 67:1658–1662 (1993).

Two of the binding sites in the upstream region correspond to recognition sites for activator proteins that are lymphoid cell specific (or highly enriched in T cells) and are shared with the promoter of the T cell receptor (TCRα) gene: these are the Ets-1 and LEF-1 transcription factors. The essential role of the upstream region has been reproduced in vitro (Sheridan, P. L., et al., *Genes Dev.*, 9:2090–2104 (1995)). LEF-1 and Ets-1 are believed to act in concert to prevent nucleosome-mediated repression in vivo. Inhibition of formation of this complex may represent a viable target for HIV-1 therapy. LEF-1 belongs to the HMG family of proteins and binds DNA as a monomer in the minor groove, resulting in a large distortion of the DNA helix (unwinding and bending) (Love, J. J., et al., *Nature*, 376:791–795 (1995)).

In addition, LEF-1 possesses a strong transactivation domain that retains its function when engineering into other DNA-binding proteins (Giese, K., et al., *Genes Dev.*, 9:995–1008 (1995)).

The HIV-1 promoter also contains tandem binding sites for NF-κB, a factor that is strongly induced by HIV infection (Bachelerie, F., et al., *Nature,* 350:709–712 (1991)), and multiple binding sites for the general transcription factor Sp1. NF-κB contacts both Sp1 and the TBP subunit of the basal transcription factor TFIID. Perkins, N. D., et al., *Mol. Cell. Biol.,* 14:6570–6583 (1994). Additionally, Sp1 has been shown to interact with the TAF110 subunit of TFIID (110 kDa TBP-associated factor) (Chen, J. L., et al., *Cell,* 79:93–105, 1994). The binding of TFIID via the TBP interaction with the TATA element nucleates the assembly of the complete RNA polymerase II transcription complex (reviewed in Maldonado, E and D. Reinberg, *Current Opinion in Cell Biology,* 7:352–361, 1995). Thus, NF-κB may function through recruitment of Sp1 and TFIID to the HIV-1 promoter via these protein-protein interactions. Accordingly, blocking the NF-κB-DNA and/or Sp1-DNA interaction is another target for HIV therapy.

Since these factors, and especially Sp1 and TFIID, are utilized for the expression of a wide range of cellular genes, the binding sites for these factors are not ideal targets for HIV-specific inhibition (or any gene-specific inhibition). However, the sequences adjacent to these sites that are unique to HIV-1 proviral DNA are excellent candidate targets for the design of inhibitory cyclic compounds.

Organisms suitable for administration of cyclic compounds according to the invention include any plant or animal containing, or suspected to contain, a gene the expression of which would be desirable to modulate. Preferred animals include mammalian, fish, and avian species. Particularly preferred mammals include humans and bovine, canine, equine, feline, ovine, and porcine animals. Particularly preferred avian and fish species are those of commercial or ecological significance. Preferred plants include commercially or ecologically significant trees, grains, grasses, and cereals.

C. Diagnostics

Cyclic compounds according to the present invention are also useful for detecting the presence of double-stranded nucleic acid, particularly dsDNA, containing a specific sequence of nucleotide base pairs for diagnostic or preparative purposes. For example, a sample containing dsDNA can be contacted by a sequence-specific cyclic compound linked to a solid substrate, thus enabling isolation of dsDNA comprising the desired sequence. Alternatively, cyclic compounds linked to a suitable detectable marker, such as biotin, a hapten, a radioisotope, or a dye molecule, can be contacted by a sample containing dsDNA suspected to contain the desired target nucleotide base pair sequence. Such bifunctional compounds complexed to dsDNA can then be detected using an appropriate detection system known to those skilled in the art. For example, DNA associated with a cyclic polyamide linked to biotin can be detected by a streptavidin/alkaline phosphatase system.

Other diagnostic applications the cyclic compounds according to the invention include double-stranded nucleic acid, particularly dsDNA, sequencing on a solid support comprising a plurality of cyclic compounds specific for different nucleotide base pair sequences.

The present invention also provides diagnostic systems, preferably in kit form, comprising cyclic compounds according to the invention. Representative embodiments of such systems include kits for assaying for the presence in a cell or tissue sample of a dsDNA sequence bound by a particular cyclic compound according to the invention. Such systems include, in an amount sufficient to perform at least one assay, one or more specific cyclic compounds (e.g., a cyclic polyamide) according to the invention as a separately packaged reagent. Instructions for use of the packaged reagent(s) are also typically included. As used herein, the term "package" refers to a solid matrix or material such as glass, plastic (e.g., polyethylene, polypropylene, or polycarbonate), paper, foil, and the like capable of holding within fixed limits such cyclic compound(s). Thus, for example, a package can be a glass vial used to contain milligram quantities of a contemplated cyclic compound, a microliter plate well to which microgram quantities of a contemplated cyclic compound have been operatively affixed, i.e., linked so as to be capable of being bound by the target sequence in dsDNA, or a glass slide to which a plurality (i.e., more than one, and to 100,00 or more) of such cyclic compounds are operatively affixed, as may be the case in certain nucleic acid sequencing methods using the instant cyclic compounds. When necessary, such diagnostic systems preferably also include a detectable label or other indicator capable of signaling the binding of the contemplated cyclic compound to its target sequence. As noted above, numerous detectable labels, such as biotin, and other indicators, such as enzyme-linked (direct or indirect) streptavidin, are well known in the art.

D. Research Reagents

The cyclic compounds described herein will also find utility as research reagents. For example, administration of such compounds to cultured cells will enable the production of cells having desired phenotypes. Such phenotypes may be useful for a variety of purposes, including the study of the effects of other compounds on the expression levels of one or more genes. Alternatively, cyclic compounds according to the invention can also be used to produce "knock-out" mutations wherein actual changes at the genetic level are unnecessary.

Cyclic compounds according to the invention will also find use in in vitro research applications. For example, addition of a cyclic compound that inhibits binding of a restriction enzyme to its cognate restriction site will prevent cleavage of a particular DNA containing such restriction site. In another example, in vitro transcription systems can be regulated by the addition of one or more appropriate cyclic compounds, particularly cyclic polyamides.

EXAMPLES

The following examples below are non-limiting and are offered merely for purposes of illustrating the practice of certain preferred embodiments of the invention herein described, specifically the design, synthesis, and testing of two representative 8 ring cyclic polyamide compounds. Illustration of the techniques described in the examples and in the detailed description above may be found in any of several well-known references, such as: Sambrook, J., et al., *Molecular Cloning: A Laboratory Manual,* Cold Spring Harbor Laboratory Press (1989); Goeddel, D., ed., *Gene Expression Technology, Methods in Enzymology,* 185, Academic Press, San Diego, Calif. (1991); "Guide to Protein Purification" in Deutshcer, M. P., ed., *Methods in Enzymology,* Academic Press, San Diego, Calif. (1989); Innis, et al., *PCR Protocols: A Guide to Methods and Applications,* Academic-Press, San Diego, Calif. (1990); Freshney, R. I., *Culture of Animal Cells: A Manual of Basic Technique,* 2$^{nd}$ Ed., Alan Liss, Inc. New York, N.Y. (1987); Murray, E. J., ed., *Gene Transfer and Expression Protocols,* pp. 109–128, The Humana Press Inc., Clifton, N.J. and Lewin, B., *Genes VI,* oxford University Press, New York (1997).

Example 1

Synthesis of Cyclic, 8-Ring Polyamides

This example describes the synthesis of several cyclic, 8-ring polyamides that bind with high affinity and specificity to 6 bp target sites through DNA-polyamide interactions in the minor groove of dsDNA. To optimize the cyclic polyamide motif, at least one chiral linker was used to cyclize two polyamide subunits each comprised of 4-rings. Specifically, substitution of the prochiral, a-position of the γ-turn residue to provide (R)-2,4,-diaminobutyric acid ((R)$^{H,N}$γ) yielded chiral cyclic polyamides with enhanced DNA-binding affinity, sequence specificity, and orientation preference. The polyamides described below can be described as follows: cyclo-(γ-Im-Py-Py-Py-(R)$^{H,N}$γ-Im-Py-Py-Py-) (3) and cyclo-(γ-Im-Py-Py-Py-(R)$^{H,N}$γ-Py-Py-Py-Py-) (4). Cyclic polyamides (3) and (4) differ by a single amino acid substitution (underlined), and each recognize a different specific 6 bp match site, i.e., 5'-AGTACT-3' and 5'-AGTATT-3', respectively, which match sites differ from one another by a single base pair (underlined). Thus, the match site for one of these polyamides can serve as a single base pair mis-match site for the other polyamide.

As controls, the binding affinities and sequence specificities of the Im-Py-Py-Py-β-Dp (1) unlinked 2:1 dimer and a hairpin analog 1m-Py-Py-Py-(R)$^{H,N}$γ-Im-Py-Py-Py-C3-OH (2) were also studied. An EDTA analogue, cyclo-(γ-Im-Py-Py-Py-(R)$^{EDTA-FE(II)}$γ-Py-Py-Py-Py-) (4-E•Fe(II)) was constructed to confirm the binding orientation of cyclic polyamide (4) at its 5'-AGTATT-3' match and 5'-AGTACT-3' single base pair mismatch site. All polyamides were synthesized by solid phase methods (see Baird, et al., *J. Am. Chem. Soc.,* vol. 118:6141 (1996), and U.S. Ser. No. 08/607,078 for a description of solid phase synthesis methods for non-cyclic polyamides). Polyamide purity and identity was confirmed by H NMR, MALDI-TOF MS, and analytical HPLC. Precise binding site sizes were determined by MPE•Fe(II) footprinting (see Van Dyke, et al., *Proc. Natl. Acad. Sci. U.S.A.,* vol. 79:5470 (1982), and Van Dyke and Dervan, *Science,* vol. 225:1122 (1984)), and binding orientation and stoichiometry confirmed by affinity cleaving experiments. See Taylor, et al., *Tetrahedron,* vol.40:457 (1984), and Dervan, P. B., *Science,* vol. 232:464 (1986). Equilibrium association constants ($K_a$) of the polyamides for their respective match and mis-match binding sites were determined by quantitative DNase I footprint titration, as described by Brenowitz, et al., *Methods Enzymol.,* vol. 130:132 (1986), Brenowitz, et al., *Proc. Natl. Acad. Sci. U.S.A.,* vol 83:8462 (1986), and Senear, et al., *Biochemistry,* vol. 25:7344 (1986).

a. Resin Synthesis

Figure 4A:
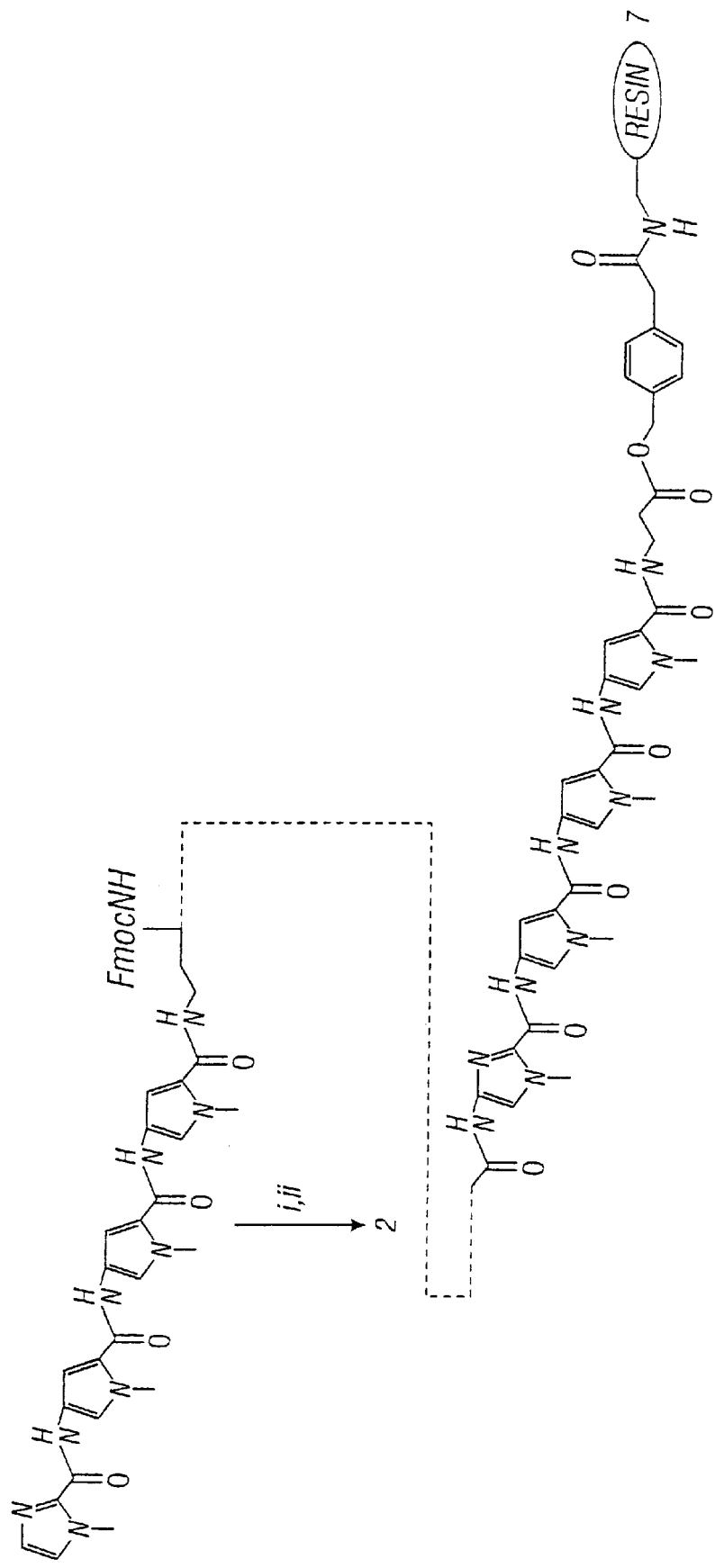
FIG. 4 shows four monomers, Boc-pyrrole-OBt ester (8)(Boc-Py-OBt), imidazole-2-Carboxylic acid2a (Boc-Im acid)(9), (R)-Fmoc-α-Boc-γ-diaminobutyric acid (10), and CBZ-γ-aminobutyric acid-imidazole dimer (Cbz-γ-Im acid) (11) (see box on FIG. 4B) for synthesis of cyclic polyamides described herein according to the following protocol: (i) 1:4 DMF:Piperidine (22° C., 30 min): (ii) LiBH4, EtOH, reflux 16 hr. (iii) 80% TFA/DCM, 0.4 M PhSH; (iv) Boc-Py-OBt, DIEA, DMF; (v): 80% TFA/DCM, 0.4 M PhSH; (vi) Boc-Py-OBt, DIEA, DMF; (vii) 80% TFA/DCM, 0.4 M PhSH; (viii) Boc-Im acid (DCC, HOBT) for 3, Boc-Py-OBt, DIEA, DMF for 4; (ix) 80% TFA/DCM, 0.4 M PhSH; (x) (R)-Fmoc-α-Boc-γ-diaminobutyric acid (HBTU, DIEA); (xi) 80% TFA/DCM, 0.4 M PhSH; (xii) Boc-Py-OBt, DIEA, DMF; (xiii) 80% TFA/DCM, 0.4 M PhSH; (xiv) Boc-Py-OBt, DIEA, DMF; (xv) 80% TFA/DCM, 0.4 M PhSH; (xvi) Boc-Py-OBt, DIEA, DMF; (xvii) 80% TFA/DCM, 0.4 M PhSH; (xviii) Cbz-γ-Im acid (HBTU, DIEA); (xix) 80% Piperdine:DMF (25° C., 30 min); (xx) Boc anhydride, DIEA, DMF; (xxi) Pd(OAc)$_2$, HCO$_2$NH$_4$, DMF (37° C., 8 hr); (xxii) DPPA, K$_2$CO$_3$ (xxiii) TFA (1 hr).
Figures 1, 4B:
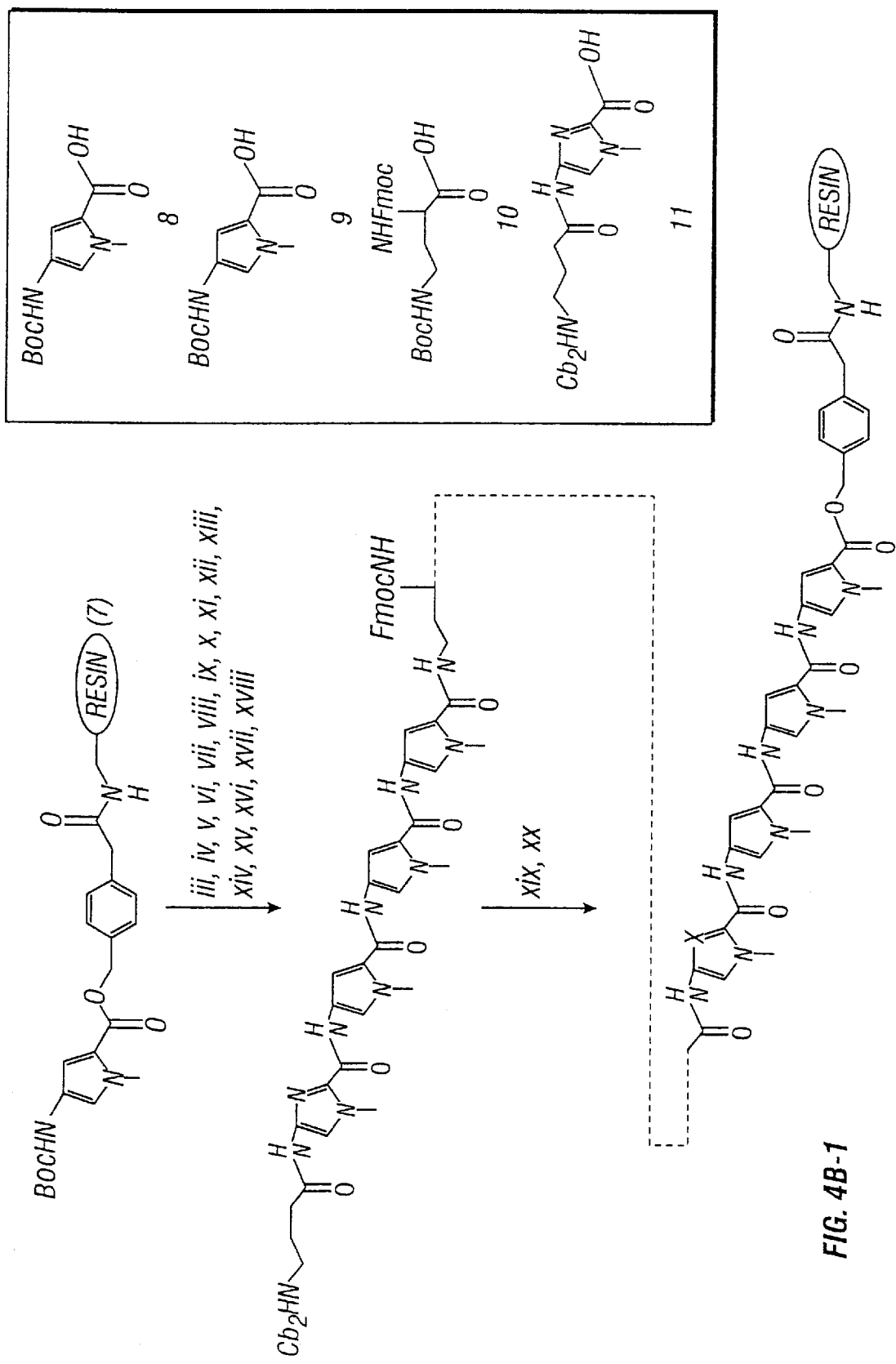
Figures 2, 4B:
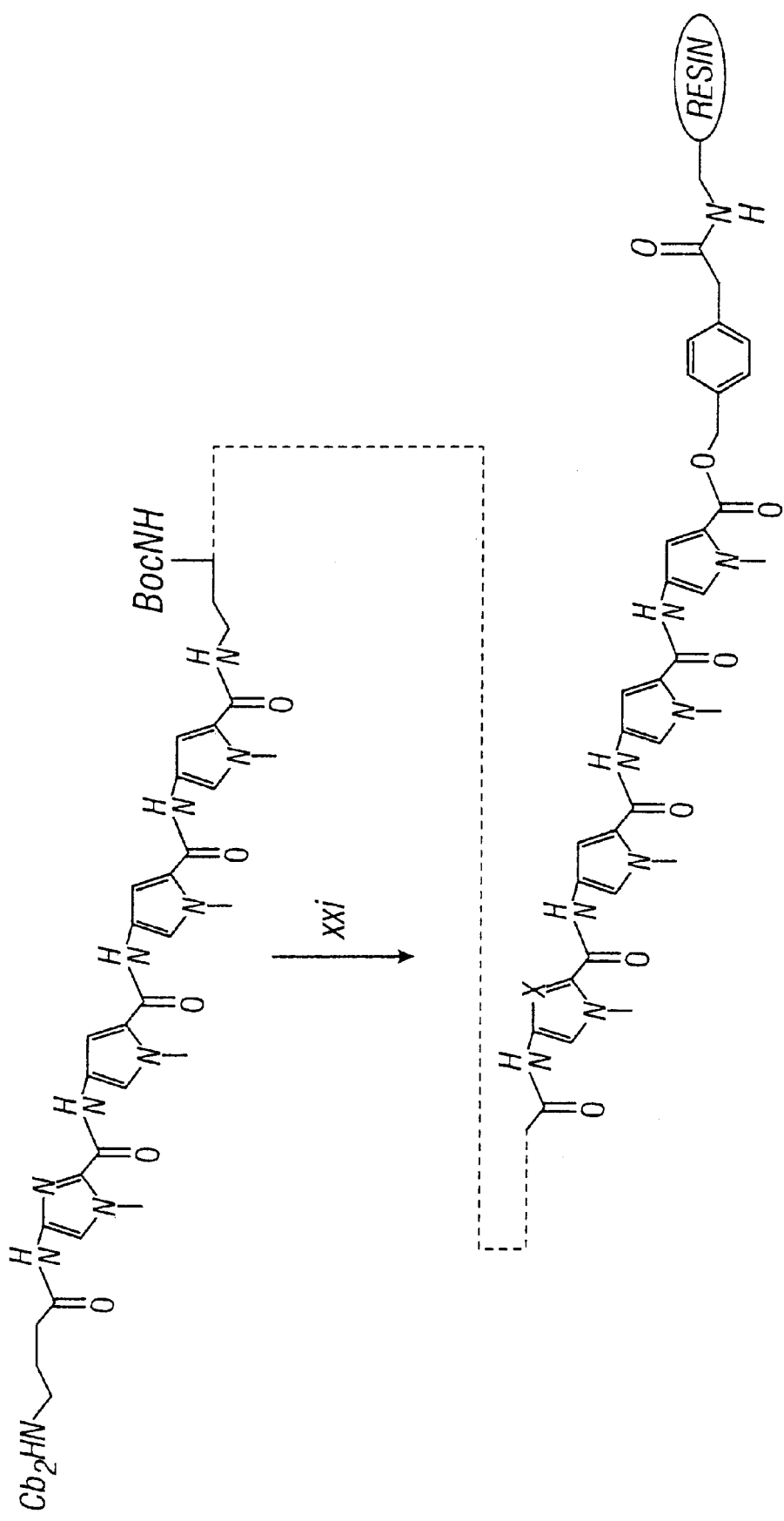
Figures 3, 4B:
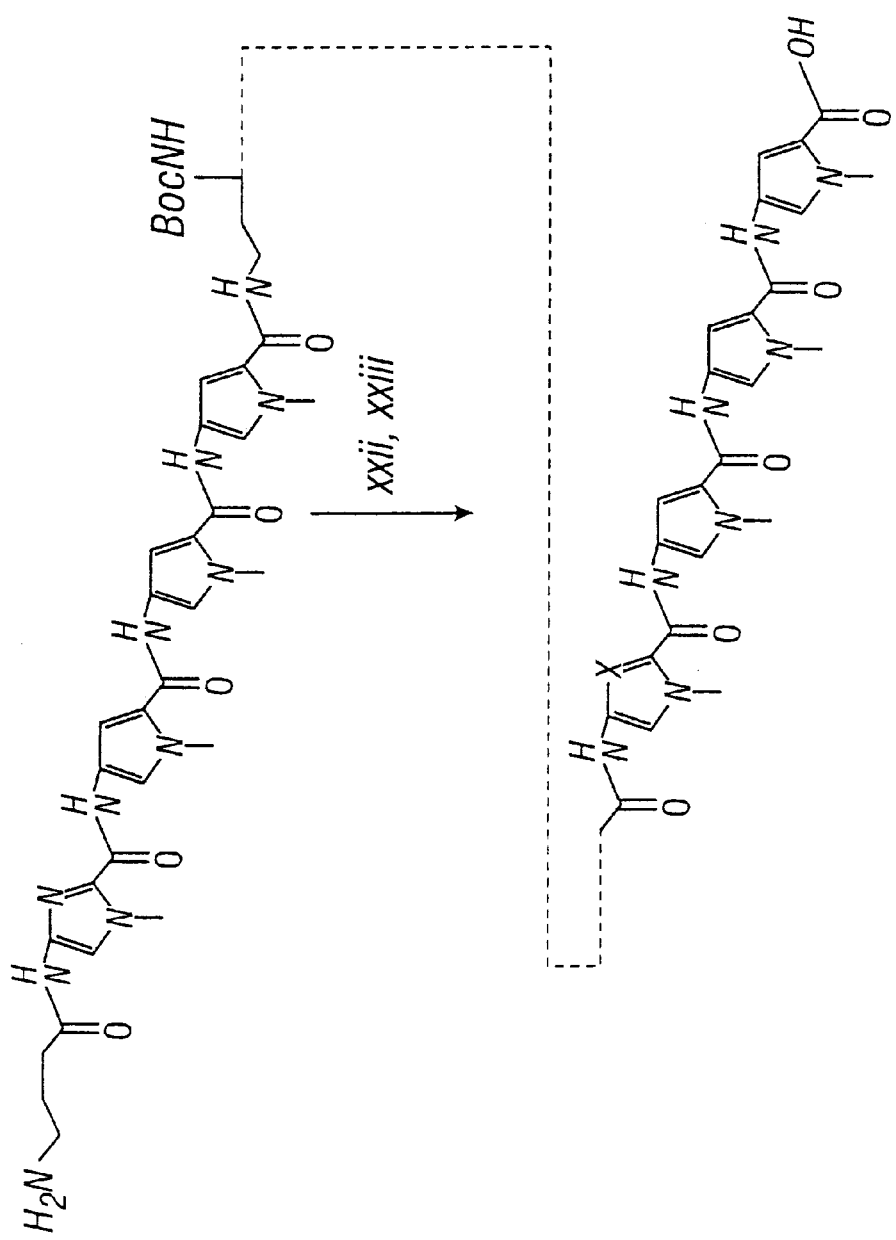

In order to prepare the cyclic polyamides, including those described herein, by solid state methods, a suitable resin is required. One such resin, comprising a Py-PAM ester (5) was prepared according to the published procedures of Mitchell, et al. (*J. Org. Chem.,* vol 43:2845 (1978)) with Boc-Py acid substituted for the standard Boc protected α-amino acid (see FIG. 2). The phenacyl ester (6) was selectively cleaved (using Zn and AcOH), and the resultant acid activated with DCC and HOBT, followed by reaction of the activated ester with an excess of 0.7 mmol/g of arninomethylated polystyrene for 24 hours (DIEA, DMF) to give Boc-Py-PAM-resin (7). Reactions were stopped at 0.1 mmol/g substitution as determined by quantitative ninhydrin analysis of free groups. See Sarin, et al.,*Anal. Biochem.,* vol. 117:147 (1981). Unreacted groups were capped by acetylation (AC$_2$O, DIEA, DMF). Picric acid titration (see Gisin, B. F., *Anal. Chim. Acta.,* vol. 58:248 (1972)) of Py-amino groups was used to verify resin loading of 0.1 mmol/g.

b. Synthesis of a Control Hairpin Polyamide

Figure 3:
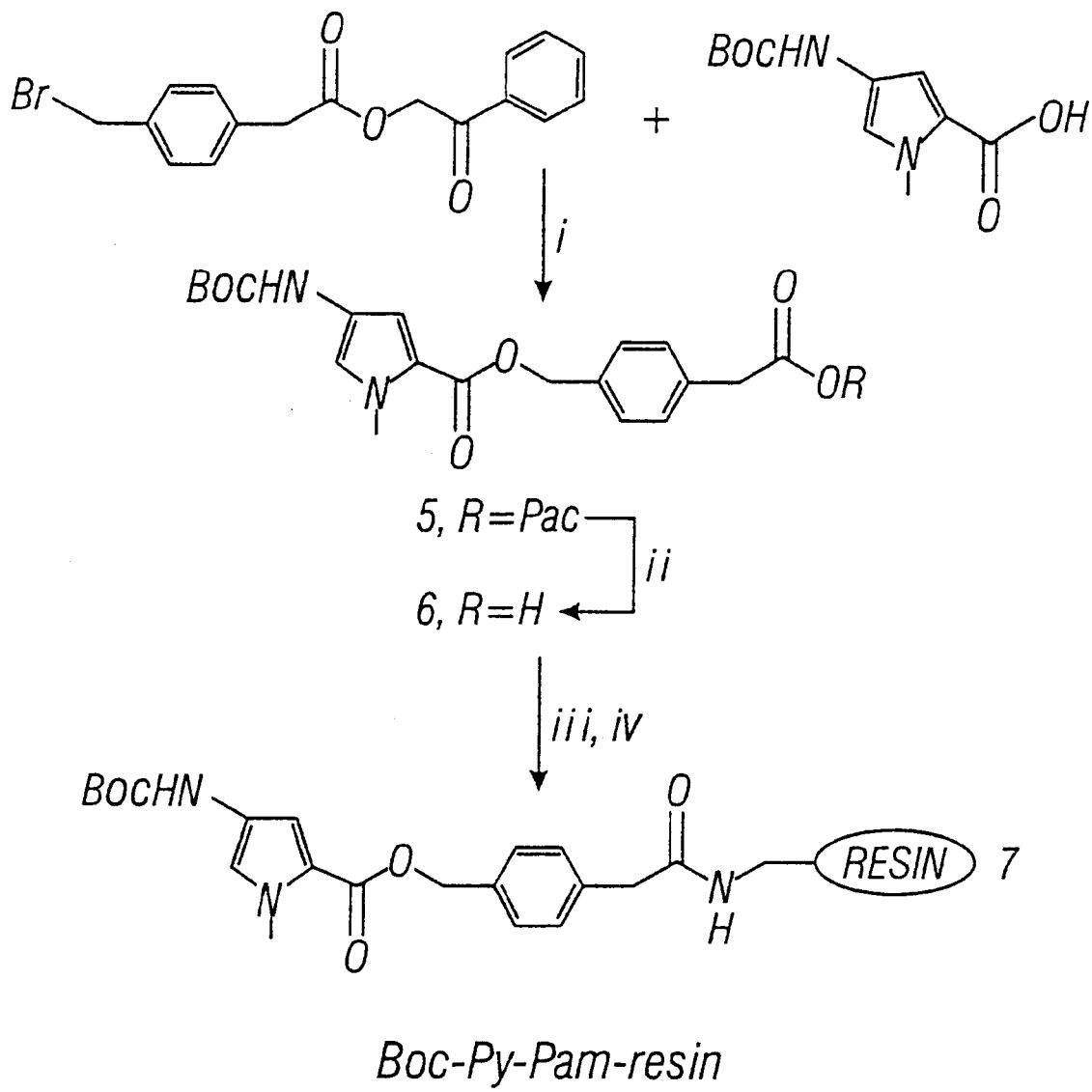
FIG. 3 depicts the synthesis of Boc-Py-PAM-resin (7) through performance of the following steps: (i) $K_2CO_3$, DMF; (ii) Zn/AcOOH, (iii) DCC/HOBT, DMF; (iv) aminomethylated-polystyrene; DIEA.

Im-Py-Py-Py-(R)$^{H,N}$γ-Im-Py-Py-Py-β-Parn resin was synthesized by machine assisted protocols in 18 steps from commercially available Boc-β-Ala-PAM resin (see FIG. 3(*a*)), according to methods described in Baird, et al.,*J. Am. Chem. Soc.,* vol. 118:6141 (1996), and U.S. Ser. No. 08/607, 078. The polyamide was cleaved from the resin by a single step reduction with lithium borohydride (EtOH, 60° C.), followed by reverse phase HPLC purification to yield the desired hairpin polyamides polyamide (2).

c. Cyclic Polyamide Synthesis

Two polyamide resins, Cbzγ-Im-Py-Py-Py-(R)$^{Fmoc}$γ-Py-Py-Py-Py-PAM resin and Cbzγ-Im-Py-Py-Py-(R)$^{Fmoc}$γ-Im-Py-Py-Py-PAM resin, were synthesized in 18 steps from the Boc-Py-PAM resin (600 mg of resin, 0.1 mmol/g of substitution) described above using machine-assisted Boc-chemistry protocols (see FIG. 3(*b*)) modified as follows: The (R)-2,4-diaminobutyric acid residue was introduced as an orthogonally protected N-α-Fmoc-N-γ-Boc derivative (10) (HBTU, DIEA). The final step was introduction of Cbzγ-Im acid (11) as a dimer block (HBTU, DIEA). See U.S. Ser. No. 08/607,078. The Fmoc-protected polyamide resins Cbzγ-Im-Py-Py-Py-(R)$^{Fmoc}$γ-Py-Py-Py-Py-PAM resin and Cbzγ-Im-Py-Py-Py-(R)$^{Fmoc}$γ-Im-Py-Py-Py-PAM resin were treated with 1:4 DMF:Piperidine (22° C., 30 min) to provide Cbzγ-Im-Py-Py-Py-(R)$^{H,N}$γ-Py-Py-Py-Py-PAM-resin and Cbzγ-Im-Py-Py-Py-(R)$^{H,N}$γ-Im-Py-Py-Py-PAM resin, respectively. The amine resins were then treated with Boc-anhydride (DIEA, DMF, 55° C., 30 min) to produce Cbzγ-Im-Py-Py-Py-(R)$^{Boc}$γ-Py-Py-Py-Py-PAM resin and Cbzγ-Im-Py-Py-Py-(R)$^{Boc}$γ-Im-Py-Py-Py-PAM resin. A single step catalytic transfer hydrogenolysis was used to cleave each polyarnide from the solid support and remove the Cbz protecting group from the N-terminal γ residue. A sample of the resin (240 mg) was treated with palladium acetate (2 ml DMF, 240 mg Pd(OAc)$_2$, 37° C., 10 min). Ammonium formate was then added (500 mg, 8 hr) and the reaction mixture purified by reverse phase HPLC to provide H$_2$Nγ-Im-Py-Py-Py-(R)$^{Boc}$γ-Py-Py-Py-Py-COOH (13) and H$_2$N-γ-Im-Py-Py-Py-(R)$^{Boc}$γ-Im-Py-Py-Py-COOH (12). Cyclization of H$_2$N-γ-Im-Py-Py-Py-(R)$^{Boc}$γ-Py-Py-Py-Py-COOH (13) and H$_2$N-γ-Im-Py-Py-Py-(R)$^{Boc}$γ-Im-Py-Py-Py-COOH (12) was achieved with DPPA and potassium carbonate, as described previously. See Cho, et al., *Proc. Natl. Acad. Sci. U.S.A.,* vol. 92:10389 (1995). The Boc-protecting group was then removed in situ by treatment with neat TFA to yield the cyclic compounds cyclo-(γ-Im-Py-Py-Py-(R)$^{H,N}$γ-Im-Py-Py-Py-) (3) and cyclo-(γ-Im-Py-Py-Py-(R)$^{H,N}$γ-Py-Py-Py-Py-) (4), followed by purification by reverse phase HPLC. The cyclic polyamides were obtained with similar yield and purity, and had similar solubility, as compared to their hairpin counterparts.

d. Binding Site Size Determination

Figures 4, 4B:
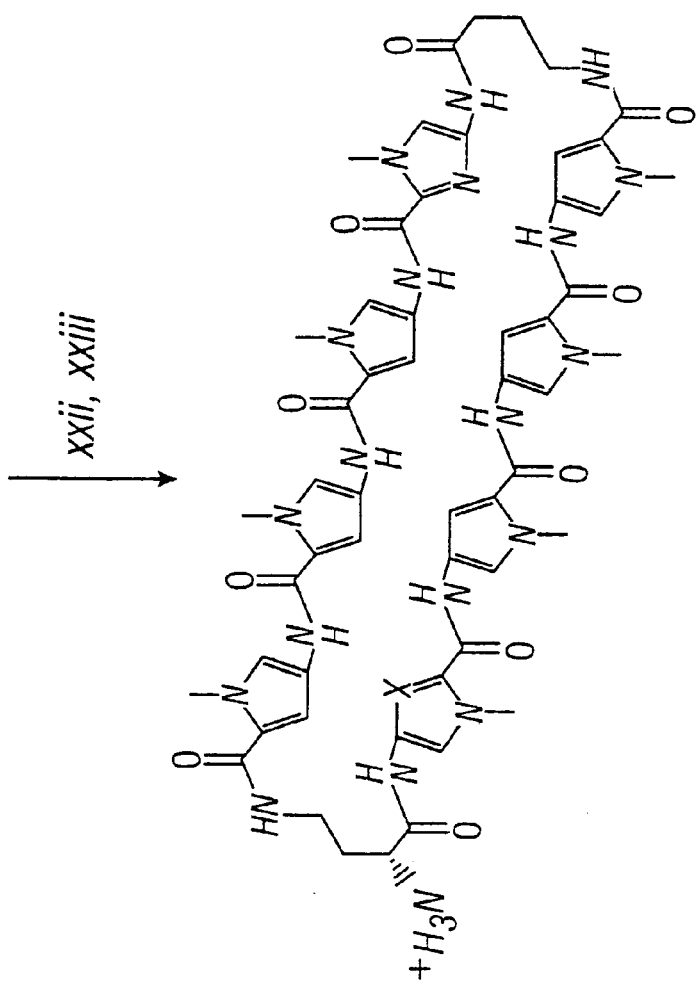
Figure 5:
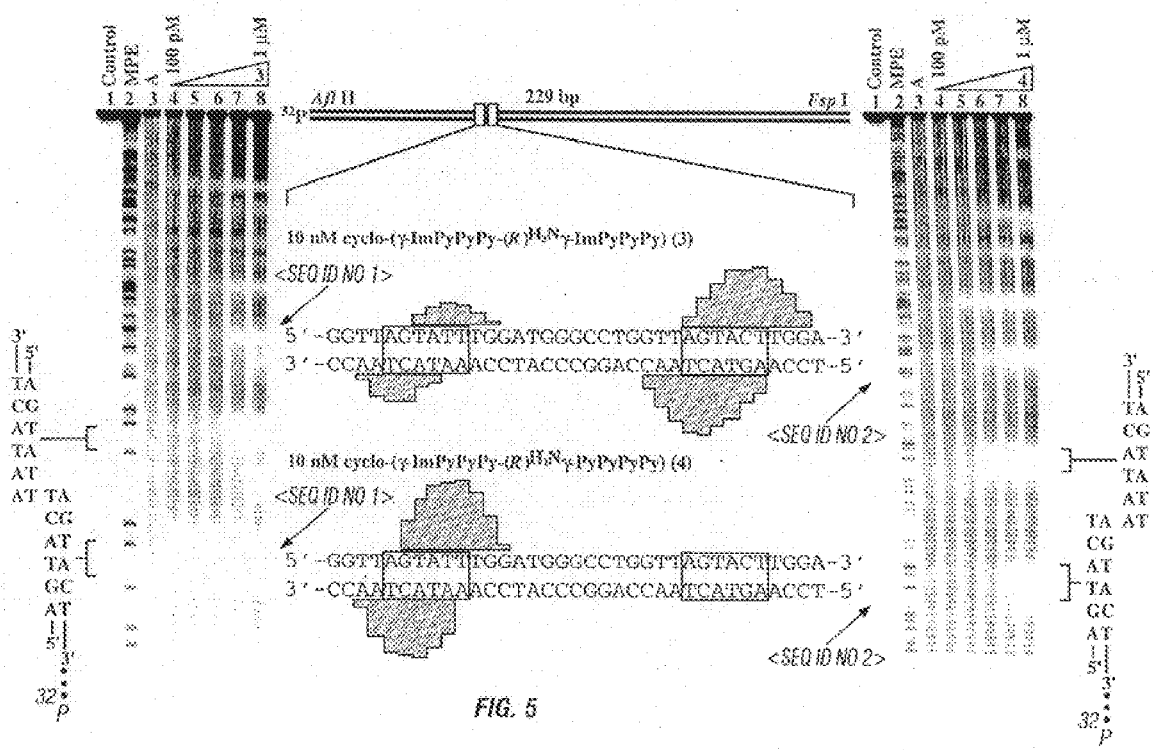
FIG. 5 illustrates the 229 bp restriction fragment with the relative positions of the match and single base pair mismatch sequences indicated for two 8-ring cyclic polyamides, cyclo-(γ-Im-Py-Py-Py-(R)$^{H_2N}$γ-Im-Py-Py-Py) (3) and cyclo-(γ-Im-Py-Py-Py-(R)$^{H_2N}$γ-Py-Py-Py-Py) (4). MPE•Fe (II) protection patterns of 10 nM cyclo-(γ-Im-Py-Py-Py-(R) $^{H_2N}$γ-Im-Py-Py-Py) (3) and 10 nM cyclo-(γ-Im-Py-Py-Py-(R)$^{H_2N}$γ-Py-Py-Py-Py) (4) are shown by the bar graphs. Bar heights are proportional to the relative protection from cleavage at each base pair. Binding sites determined by MPE•Fe(II) footprinting and quantitated by DNase I footprint titrations are boxed. Autoradiograms of MPE•Fe(II) footprinting experiments using cyclo-(γ-Im-Py-Py-Py-(R) $^{H_2N}$γ-Im-Py-Py-Py) (3) (left) and cyclo-(γ-Im-Py-Py-Py-(R) $^{H_2N}$γ-Py-Py-Py-Py) (4) (right) on the 3' $^{32}$P-labeled 229 bp restriction fragment of pJT8. 5'-AGTATT-3' and 5'-AGTACT-3' sites are shown adjacent to the auto radiograms. Lane 1, intact control; lane 2, MPE•Fe(II) reaction; lane 3, A reaction standard; lanes 4–8: 100 pM; 1 nM; 10 nM; 100 nM; and 1 mM polyamide, respectively. All lanes contain 15 kcpm of either 3' or 5'-radiolabeled DNA, 25 mM HEPES buffer (pH 7.3), 200 mM NaCl, 50 mg/ml glycogen, 5 mM DTT, 0.5 mM MPE•Fe(II), and were run at 22° C.

MPE•Fe(II) footprinting on 3' or 5'-$^{32}$P end-labeled 229 base pair restriction fragments revealed that cyclic polyamides (3) and (4), at 10 nM concentration, each bound to its designated 6 bp match sites (25 mM HEPES buffer (pH 7.3), 200 mM NaCl, 50 µg/ml glycogen, 5 mM DTT, 0.5 µM MPE•Fe(II), and 22° Q (see FIG. 4)). Cyclic polyamide, (3), which contains an Im/Py and a Py/Im pair, was found to protect the cognate 5'-AGTACT-3' match site. Binding of polyamide (3) to a single base pair mis match site (e.g., 5'-AGTATT-3') was detected only at much higher polyamide concentrations. Polyamide (4), which contains a single Im/Py pair, protected its targeted match site 5'-AGTATT-3' and the single base pair mismatch site 5'-AGTACT-3'. The sizes of the asymmetrically 3'-shifted footprint cleavage patterns were consistent with 1:1 cyclic polyamide:dsDNA complex formation at 6 bp binding sites.

e. Binding Orientation Analysis

Figure 7A:
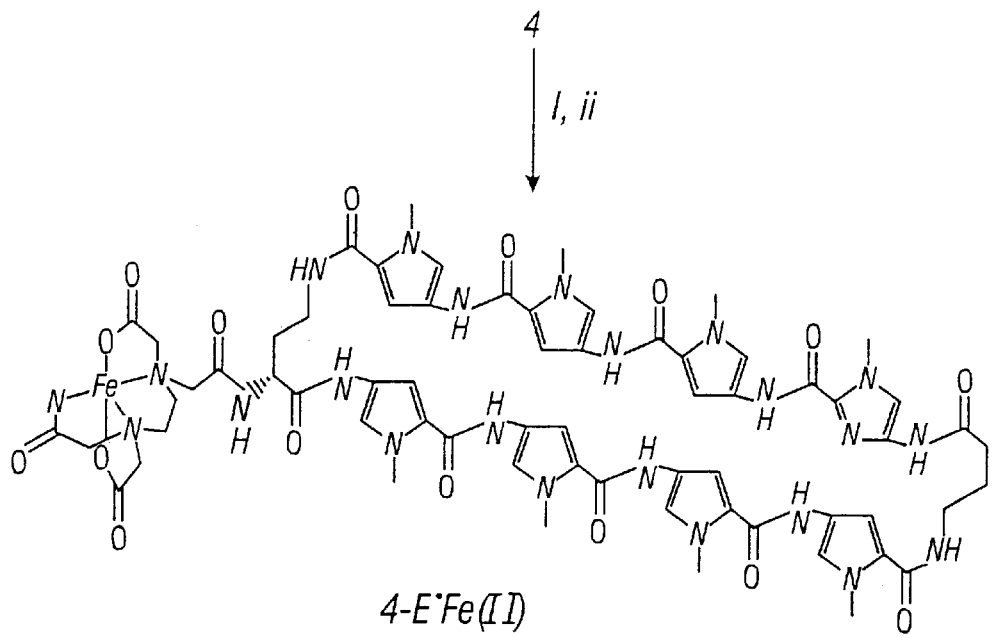
FIGS. 7A–7C illustrate the synthesis of cyclo-(γ-Im-Py-Py-Py(R)$^{EDTA•Fe(II)}$γPy-Py-Py-Py) (4-E•Fe(II)) from cyclo-(γ-Im-Py-Py-Py-(R)$^{H_2N}$γ-Py-Py-Py-Py) (4) by: (i) EDTA dianhydride (DMSO/NMP, DIEA, 55° C., 15 min); (ii) 0.1 M NaOH (55° C., 10 min). Panel (b) shows the affinity cleavage pattern for at 100 nM concentration depicting a single binding orientation at the 5'-AGTATT-3 match site and no orientational preference at the 5'-AGTACT-3' mismatch site. Panel (c) shows a ball-and-stick model of a 4-E•Fe(II)•5'-AGTATT-3' complex. Bar heights are proportional to the relative cleavage intensities at each base pair. Shaded and non-shaded circles denote Im and Py carboxamides, respectively. The boxed Fe denotes the EDTA•Fe(II) cleavage moiety.
Figure 7B:
Figure 7C:
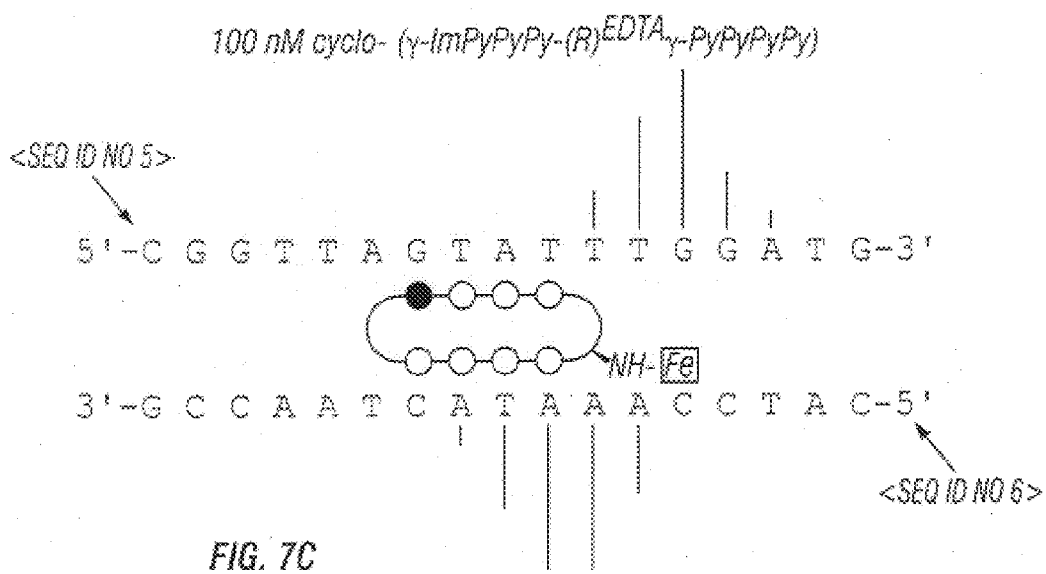

Affinity cleavage experiments using cyclo-(γ-Im-Py-Py-Py-(R)$^{EDTA \cdot Fe(II)}$γ-Py-Py-Py-Py-) (4-E•Fe(II)), which contained an EDTA•e(II) cleavage moiety appended to the chiral γ linker, were used to confirm binding orientation and stoichiometry for the cyclic polyamide. To synthesize the EDTA analogue, cyclo-(γ-Im-Py-Py-Py-(R)$^{H,N}$γ-Py-Py-Py-Py-) (4) was treated with an excess of EDTA-dianhydride (DMSO/NMP, DIEA, 55° C., 15 min) and the remaining anhydride was hydrolyzed (0.1 M NaOH, 55° C., 10 min). Cyclo-(γ-Im-Py-Py-Py-(R)$^{EDTA}$γ-Py-Py-Py-Py-) (4-E•Fe(II)) was then isolated by reverse phase HPLC (see FIGS. 6 and 7). Affinity cleavage experiments were performed on the same 3'- or 5'-$^{32}$P end-labeled 229 base pair DNA restriction fragment from the plasmid pJT8 (20 mM HEPES buffer (pH 7.3), 200 mM NaCl, 50 μg/ml glycogen, 5 mM DTT, 1 μM Fe(II), pH 7.0 and 22° C.). The observed cleavage pattern for polyamide 4-E•Fe(II) (see FIGS. 6(a) and 6(b), are 3'-shifted, a result consistent with minor groove occupancy by the cyclic polyamide. In the presence of 100 nM 4-E•Fe (II), a major cleavage locus proximal to the 3' side of the 5'-AGTATT-3' match sequence was revealed, consistent with formation of an oriented 1:1 cyclic polyamide•DNA complex. At the same ligand concentration, minor cleavage loci located 3' and 5' adjacent to the single base pair mis-match 5'-AGTACT-3' site appeared, consistent with dual binding orientations at this symmetrical binding site. The cyclic polyamide binding model was further supported by the location of cleavage loci at the 5' side of the 5'-AGTATT-3' match site, and at the 5' and 3' sides of the 5'-AGTACT-3' mismatch site corresponding to the EDTA•Fe(II) moiety placement off the ((R)$^{H,N}$γ) linker.

f. Binding Energetics

Figure 8A:
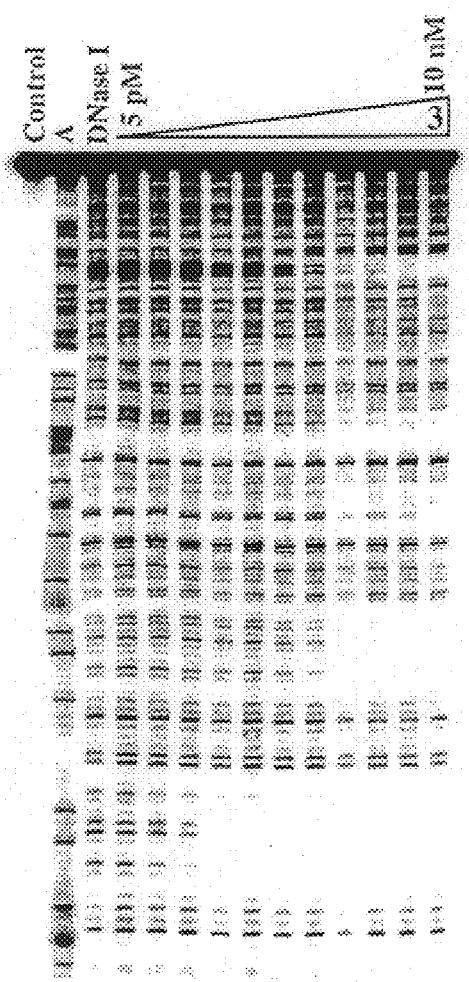
FIGS. 8A and 8B depict the results quantitative DNase I footprint titration experiments with (a) cyclo-(Γ-Im-Py-Py-Py-(R)$^{H_2N}$γ-Im-Py-Py-Py) (3) and (b) cyclo-(γ-Im-Py-Py-Py (R)$^{H_2N}$γ-Py-Py-Py-Py) (4) on the 3'-end labeled 229-bp restriction fragment of pJT8. Lane 1, intact DNA control; lane 2, A reaction; lane 3, DNase I standard, lanes 4–13, 5 pM, 10 pM, 20 pM, 50 pM, 100 pM, 1 nM, 2 nM, 5 nM, and 10 nM of the respective polyamide. The 5'-AGTACT-3' and 5'-AGTATT-3' match and mis-match sites for each polyamide were analyzed and are shown on the right side of the respective autoradiograms. All reactions contained 20 kcpm of radiolabeled restriction fragment, 10 mM Tris•HCI (pH 7.0), 10 mM KC1, 10 mM MgCl$_2$, and 5 mM CaCl$_2$.
Figure 8B:
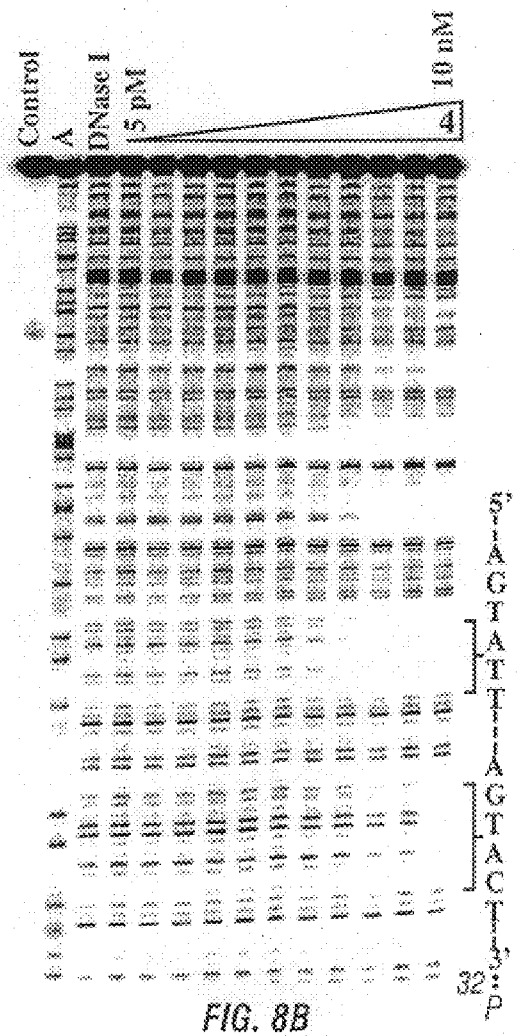

Quantitative DNase I footprint titrations (10 mm Tris•HCl, 10 mM KCl, 10 MM MgCl$_2$ and 5 mM CaCl$_2$ pH 7.0 and 22° C.) were performed to determine the equilibrium association constants (K$_a$) of Im-Py-Py-Py-β-Dp (1), Im-Py-Py-Py-(R)$^{H,N}$γIm-Py-Py-Py-OH (2), cyclo-(γ-Im-Py-Py-Py-(R)$^{H,N}$γ-Im-Py-Py-Py) (3), and cyclo-(γ-Im-Py-Py-Py-(R)$^{H,N}$γ-Py-Py-Py-Py-) (4) for the 6 bp match and mis-match sites. The results for (3) and (4) are depicted in FIG. 8.

Unlinked polyamide (1) bound its respective match and mis-match sites with an apparent first order association constant (eq 2, n=2), consistent with 2:1 dimer formation. Hairpin polyamide (2) and cyclic polyamides (3) and (4) bound to their respective match and mis-match sequences with binding isotherms (eq 2, n=1) consistent with binding in a 1:1 polyamide•DNA complex. Polyamides bound the 5'-AGTACT-3' site with decreasing affinity, in the following order: match cyclic polyamide (3) >match hairpin polyamide (2) >mismatch cyclic polyamide (4) >match unlinked, dimeric polyamide (1). Polyamides bound the 5'-AGTATT3' target, sequence with affinities that decreased in the following order: match cyclic polyamide (4) >mis-match cyclic polyamide (3) >mis-match hairpin polyamide (2) >mis-match unlinked, dimeric polyamide (1).

Covalent coupling of unlinked, dimeric polyamide (1) to form hairpin polyamide (2) resulted in a 428-fold increase in the dsDNA binding affinity and comparable DNA binding sequence specificity. It is interesting to compare hairpin polyamide (2), Im-Py-Py-Py-(R)$^{H,N}$γ-Im-Py-Py-Py-OH, to the previously reported hairpin Im-Py-Py-Py-γ-Im-Py-Py-Py-β-Dp. Each hairpin contains eight aromatic rings and a single C-terminal charge located either on the γ linker or a C-terminal β-Dp group. Although hairpin polyamide (2) binds to DNA with an affinity and specificity comparable to DNA-binding proteins, it binds with 4-fold lower affinity and 5-lower sequence specificity than the previously described hairpin Im-Py-Py-Py-γ-Im-Py-Py-Py-β-Dp. This probably results from the loss of structure that provides for favorable interactions between the β-Dp group and A,T rich sequences flanking the target site. Since cyclic polyamides lack any C-terminal β-Dp group, hairpin polyamide (2) was determined to be a more suitable control for the studies herein described.

On the basis of the pairing rules for polyamide•DNA complexes, the 5'-AGTACT-3' and 5'-AGTATT-3' target sites represented "match" and "single base pair mis-match" sites for cyclic polyamide (3) respectively, and single base pair mis-match and match sites for cyclic polyamide (4), respectively. Cyclic-polymide (3) was determined to bind to its match 6 bp target sequence, 5'-AGTACT-3', with an equilibrium association constant of K$_a$=7.6×10$^{10}$ M$^{-1}$, and 55-fold specificity over the single base pair mis-match site 5'-AGTATT-3' site (K$_a$=1.3×10$^9$ M$^{-1}$). These affinities represented a 3,600-fold increase relative to the unlinked, dimeric polyamide formed by polyamide (1), and an 8-fold enhancement relative to hairpin polyamide (2). Furthermore, the affinity and specificity of cyclic polyamide (3) were comparable to the previously described hairpin Im-Py-Py-Py-γ-Im-Py-Py-Py-β-Dp. The cyclic polyamide (4), cyclo-(γ-Im-Py-Py-Py-(R)$^{H,N}$γ-<u>Py</u>-Py-Py-Py-), which contains a single Im/Py pair, preferentially bound its match site, 5'-AGTATT-3', with an affinity of K$_a$=3.1×10$^9$ M$^{-1}$, versus the single base pair mis-match site 5'-AGTA<u>C</u>T-3' (K$_a$=4.2× 10$^8$ M$^{-1}$) with a 7-fold preference. Therefore, replacing a single pyrrole amino acid in cyclo-(γ-Im-Py-Py-Py-(R)$^{H,N}$γ-<u>Py</u>-Py-Py-Py) (4) with an imidazole residue to make cyclo-(γ-Im-Py-Py-Py-(R)$^{H,N}$γ-<u>Im</u>-Py-Py-Py-) (3), regulated cyclic polyamide specificity and affinity by 2 orders of magnitude.

The representative cyclic polyamides described above were capped at the N-terminus of each polymer portion in order to complete the cycle. However, N-terminal acetylation has been found to reduce hairpin polyamide binding specificity and orientation preference. See White, et al., *J. Am. Chem. Soc.*, vol. 119:8756–8765 (1997), and Parks, et al., *J. Am. Chem. Soc.*, vol. 118:6147–6152 (1996). Like hairpin polyamides, cyclic polyamides are capable of forming two mirror image folded structures, only one of which is responsible for 5'→3', N→C match site binding to dsDNA. See White, et al., *J. Am. Chem. Soc.*, vol. 119:8756–8765 (1997). While not wishing to be bound to a particular theory, it is likely that the chiral amine group in one or more of the linkers can help to offset any 'acetylation effect' by controlling cyclic polyamide binding orientation preference, and hence binding specificity. It is also clear from the above data that the clear from comparison of the 3- and 4-ring cycles, that the detailed rules which have been developed to guide polyamide design have to be carefully considered for successful discovery and evaluation of useful Hp-Im-Py polyarnide binding motifs.

One skilled in the art will readily appreciate that the present invention is well adapted to carry out the objects and obtain the ends and advantages mentioned, as well as those inherent, therein. The compounds, methods, treatments, procedures, and applications described herein are presently representative of preferred embodiments, and are exemplary and not intended as limitations on the scope of the invention. Changes, modifications, and alternatives therein and other uses will occur to those skilled in the art upon review of the above description, which changes are encompassed within the spirit of the invention and the appended claims.

The invention illustratively described herein suitably may be practiced in the absence of any element or elements, or limitation or limitations, which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed.

All patents, patent applications, and other publications and references mentioned in the specification are hereby incorporated by reference in their entirety, and are indicative of the levels of those skilled in the art to which the invention pertains.

We claim:

1. A cyclic compound comprising from seven to twenty aromatic carboxamide units, one or more of which is a hydrogen bond donor or acceptor, which cyclic compound forms nucleotide base pair-specific interactions with a double-stranded nucleic acid molecule under physiological conditions, but excluding cyclo-(Im-Py-Im-Py-γ-Im-Py-Im-Py-(G-Dp)γ), cyclo(Im-Py-Im-Py-γ-Im-Py-Im-Py-(G-Dp)), and cyclo(Im-Py-Py-Py-γ-Im-Py-Py-Py-(G-Dp)), wherein Im is N-methylimidazole, Py is N-methylpyrrole, G is glycine, γ is γ-aminobutyric acid, and Dp is dimethylaminopropylamide.

2. The cyclic compound according to claim 1 wherein the compound comprises a first polymer comprising at least three aromatic carboxamide units, which first polymer is linked to a second polymer comprising at least four aromatic carboxamide units.

3. The cyclic compound according to claim 2 wherein the first polymer comprises at least four aromatic carboxamide units.

4. The cyclic compound according to claim 3 wherein each of the hydrogen bond donors is an aromatic carboxamide unit.

5. The cyclic compound according to claim 4 wherein the first and second polymers comprise equal numbers of aromatic carboxamide units.

6. The cyclic compound according to claim 1 wherein each aromatic carboxamide unit comprises an aromatic ring having 5 or 6 ring atoms.

7. The cyclic compound according to claim 6 wherein the ring atoms of each aromatic carboxamide unit are independently selected from the group consisting of carbon, nitrogen, sulfur, and oxygen.

8. The cyclic compound according to claim 4 wherein the aromatic carboxamide units of the first and second polymers are selected from the group consisting of imidazole, pyrrole, and hydroxypyrrole carboxamides.

9. The cyclic compound according to claim 5 wherein each hydrogen bond donor of the first polymer aligns with a hydrogen bond donor of the second polymer to form a donor pair that preferably associates under physical conditions with at least one, but not all, nucleotide base pairs selected from the group consisting of A/T, T/A, G/C and C/G.

10. The cyclic compound according to claim 2 wherein said first and second polymers are linked via a linker having the formula —NH—(CH$_2$)$_n$—C(O)O—, wherein n is 2 or 3,
and wherein one or more methylene hydrogens are optionally replaced by a substituent group.

11. The cyclic compound according to claim 2 wherein said first and second polymers are linked via two linkers independently having the formula —NH—(CH$_2$)$_n$—C(O)O—, wherein n is 2 or 3,
and wherein one or more methylene hydrogens are optionally replaced by a substituent group.

12. The cyclic compound according to claim 11 wherein one or both linkers is γ-aminobutyric acid.

13. The cyclic compound according to claim 12 wherein one or both γ-aminobutyric acid linkers is substituted.

14. A compound comprising a cyclic compound covalently associated with at least one second compound selected from the group consisting of a second cyclic compound, a protein, a nucleic acid, and a polyamide, wherein the cyclic compound comprises from seven to twenty aromatic carboxamide units, one or more of which is a hydrogen bond donor or acceptor, which cyclic compound forms nucleotide base pair-specific interactions with a double-stranded nucleic acid molecule under physiological conditions, but excluding cyclo(Im-Py-Im-Py-γ-Im-Py-Im-Py-(G-Dp)-γ), cyclo(Im-Py-Im-Py-γ-Im-Py-Im-Py-(G-Dp)), and cyclo(Im-Py-Py-Py-γ-Im-Py-Py-Py-(G-Dp)), and wherein Im is N-methylimidazole, Py is N-methylpyrrole, G is glycine, γ is γ-aminobutyric acid, and Dp is dimethylaminopropylamide.

15. The compound according to claim 14 wherein the second compound is a polyamide selected from the group consisting of a hairpin polyamide molecule, an H-pin polyamide molecule, extended polyamide molecule, and an overlapped polyamide molecule.

16. The compound according to any one of claim 1, 2, 3, 4–5, 6–11 or 12–15 that binds with subnanomolar affinity to a target nucleic acid sequence in a double-stranded nucleic acid molecule.

17. The compound according to claim 16 that binds to a target nucleotide base pair sequence with a binding affinity that is at least 2-fold greater than a second binding affinity of said compound to a non-target nucleotide base pair sequence.

18. The compound according to claim 16 that associates under physiological conditions with a minor groove of a double-stranded nucleic acid molecule.

19. A cyclic compound of from seven to 20 aromatic carboxamide units comprising a first polymer comprising at least three aromatic carboxamide units which are hydrogen bond donors, which first polymer is linked to a second polymer comprising at least four aromatic carboxamide units which are hydrogen bond donors, wherein the cyclic compound has a molecular structure that forms nucleotide base pair-specific interactions with a double-stranded nucleic acid molecule under physiological conditions.

20. A composition comprising a carrier and the compound according to any one of claim 1, 2, 3, 4, 5, or 6–11, 12 or 13.

21. A cyclic compound according to claim 1 or 19, wherein said cyclic compound binds with a $K_d$ of less than 100 nM under physiological conditions to a specific target sequence of from four to twenty nucleotide base pairs in a double-stranded nucleic acid, wherein said $K_d$ is at least 2-fold less than a second $K_d$ of said cyclic compound to a non-target nucleotide base pair sequence of the same length as the specific target sequence.

22. A cyclic compound comprising:

a first polymer and a second polymer, said first polymer having the structure

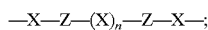

said second polymer having the structure

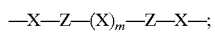

wherein each X is an independently selected aromatic carboxamide unit, each Z is a covalent linkage between adjacent aromatic carboxamide units, n and m are selected such that, combined, said first and second polymers contain from seven to 20 aromatic carboxamide units, provided that n is at least 1 and m is at least 2, and the first and second polymers are linked by two linkers extending between the first and second polymers to produce a cyclic compound having a molecular structure that forms nucleotide base pair-specific interactions with a double-stranded nucleic acid molecule under physiological conditions.

23. A composition comprising a carrier and the compound according to claim 22.

24. The cyclic compound according to claim 1, further comprising at least one non-aromatic carboxamide unit.

25. The cyclic compound according to claim 24, comprising at least one glycine or β-alainine carboxamide unit.

* * * * *

SEQUENCE LISTING

```
<160> NUMBER OF SEQ ID NOS: 6

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ggttagtatt tggatgggcc tggttagtac ttgga                                35

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tccaagtact aaccaggccc atccaaatac taacc                                35

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gttagtattt ggatgggcct ggttagtact tgga                                 34

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tccaagtact aaccaggccc atccaaatac taac                                 34

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cggttagtat ttggatg                                                    17
```

```
<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
catccaaata ctaaccg                                                    17
```